(12) United States Patent
Fonte et al.

(10) Patent No.: US 11,504,019 B2
(45) Date of Patent: Nov. 22, 2022

(54) SYSTEMS AND METHODS FOR MONITORING AND UPDATING BLOOD FLOW CALCULATIONS WITH USER-SPECIFIC ANATOMIC AND PHYSIOLOGIC SENSOR DATA

(71) Applicant: HeartFlow, Inc., Redwood City, CA (US)

(72) Inventors: Timothy A. Fonte, San Francisco, CA (US); Leo Grady, Millbrae, CA (US); Charles A. Taylor, Atherton, CA (US)

(73) Assignee: HeartFlow, Inc., Redwood City, CA (US)

(*) Notice: Subject to any disclaimer, the term of this patent is extended or adjusted under 35 U.S.C. 154(b) by 352 days.

(21) Appl. No.: 15/708,980

(22) Filed: Sep. 19, 2017

(65) Prior Publication Data

US 2018/0078149 A1    Mar. 22, 2018

Related U.S. Application Data

(60) Provisional application No. 62/397,133, filed on Sep. 20, 2016.

(51) Int. Cl.
*A61B 5/026* (2006.01)
*A61B 5/11* (2006.01)
(Continued)

(52) U.S. Cl.
CPC ............ *A61B 5/026* (2013.01); *A61B 5/0022* (2013.01); *A61B 5/02007* (2013.01);
(Continued)

(58) Field of Classification Search
CPC .. G16H 10/00–65; G16H 80/00; G16H 40/00; G16H 40/40; G16H 40/60;
(Continued)

(56) References Cited

U.S. PATENT DOCUMENTS 7,129,836 B2\* 10/2006 Lawson ................. G16H 40/67
705/2
8,157,742 B2    4/2012 Taylor
(Continued)

FOREIGN PATENT DOCUMENTS

JP        2016146958 A      8/2016

OTHER PUBLICATIONS

Mukhopadhyay, Subhas Chandra. "Wearable sensors for human activity monitoring: A review." IEEE sensors journal 15.3 (2014): 1321-1330. (Year: 2014).\*

(Continued)

*Primary Examiner* — David J. McCrosky
(74) *Attorney, Agent, or Firm* — Bookoff McAndrews, PLLC

(57) ABSTRACT

Systems and methods are disclosed for informing and monitoring blood flow calculations with user-specific activity data, including sensor data. One method includes receiving or accessing a user-specific anatomical model and a first set of physiological characteristics of a user; calculating a first value of a blood flow metric of the user based on the user-specific anatomical model and the first set of physiological characteristics; receiving or calculating a second set of physiological characteristics of the user by accessing or receiving sensor data of the user's blood flow and/or sensor data of the user's physiological characteristics; and calculating second value of the blood flow metric of the user based on the user-specific anatomical model and the second set of physiological characteristics of the user.

20 Claims, 7 Drawing Sheets

(51) Int. Cl.
*G06F 16/00* (2019.01)
*G16H 50/50* (2018.01)
*A61B 5/00* (2006.01)
*A61B 5/02* (2006.01)
*G16H 50/30* (2018.01)
*G16H 50/70* (2018.01)
*G16H 10/40* (2018.01)
*A61B 8/06* (2006.01)

(52) U.S. Cl.
CPC .......... *A61B 5/1118* (2013.01); *A61B 5/7275* (2013.01); *A61B 8/06* (2013.01); *G06F 16/00* (2019.01); *G16H 10/40* (2018.01); *G16H 50/30* (2018.01); *G16H 50/50* (2018.01); *G16H 50/70* (2018.01); *A61B 5/681* (2013.01); *A61B 5/6895* (2013.01); *A61B 5/6898* (2013.01); *A61B 5/7246* (2013.01); *A61B 5/746* (2013.01)

(58) Field of Classification Search
CPC .. G16H 40/63; G16H 40/67; G16H 50/00–70; G16H 30/40; G16H 50/20; G16H 50/50; A61B 8/06; A61B 8/065; A61B 5/026–0295; A61B 34/10; A61B 2034/101; A61B 2034/102; A61B 2034/104; A61B 2034/105; A61B 2034/107; A61B 5/1112–1118; A61B 5/1123; A61B 5/1124; A61B 5/1126; A61B 8/8466; G06T 2207/30004–30104; G06T 7/0012; G06T 11/003; G06T 2207/20081; G06T 2207/20084; G06T 2207/20092–20108; G06F 30/20; G06F 30/28; G06F 19/30–3418
See application file for complete search history.

(56) References Cited

U.S. PATENT DOCUMENTS

| | | | |
|---|---|---|---|
| 8,249,815 B2 | 8/2012 | Taylor | |
| 8,311,747 B2 | 11/2012 | Taylor | |
| 8,311,748 B2 | 11/2012 | Taylor | |
| 8,311,750 B2 | 11/2012 | Taylor | |
| 8,315,812 B2 | 11/2012 | Taylor | |
| 8,315,813 B2 | 11/2012 | Taylor | |
| 8,315,814 B2 | 11/2012 | Taylor | |
| 8,321,150 B2 | 11/2012 | Taylor | |
| 8,386,188 B2 | 3/2013 | Taylor | |
| 8,872,664 B2 * | 10/2014 | Bischoff | G16H 40/67 340/573.1 |
| 9,087,147 B1 | 7/2015 | Fonte | |
| 9,202,010 B2 | 12/2015 | Taylor | |
| 2014/0073977 A1 | 3/2014 | Grady | |
| 2014/0236011 A1 | 8/2014 | Fan et al. | |
| 2014/0243663 A1 * | 8/2014 | Taylor | A61B 5/0263 600/427 |
| 2015/0102925 A1 * | 4/2015 | Foldyna | G16H 50/20 340/539.12 |
| 2015/0342537 A1 | 12/2015 | Taylor | |
| 2016/0066861 A1 | 3/2016 | Taylor | |
| 2017/0340920 A1 * | 11/2017 | Posio | A61B 5/1118 |

OTHER PUBLICATIONS

Patel, Shyamal, et al. "A review of wearable sensors and systems with application in rehabilitation." Journal of neuroengineering and rehabilitation 9.1 (2012): 1-17. (Year: 2012).*

* cited by examiner

SYSTEMS AND METHODS FOR MONITORING AND UPDATING BLOOD FLOW CALCULATIONS WITH USER-SPECIFIC ANATOMIC AND PHYSIOLOGIC SENSOR DATA

RELATED APPLICATION(S)

This application claims priority to U.S. Provisional Application No. 62/397,133 filed Sep. 20, 2016, the entire disclosure of which is hereby incorporated herein by reference in its entirety.

INTRODUCTION

Personalized anatomical and physiological models have recently been introduced into clinical practice to support the assessment and treatment of coronary artery disease. Personalized anatomical and physiological models may have limitations, for example, (1) the physiological assumptions made in anatomical and physiological model simulation calculations may not be user-specific, (2) the assumptions may remain constant, even as the user may change, and (3) the physiological assumptions may mimic test procedures that do not incorporate real-time input, e.g., actual user activity. As a result, a personalized simulation may be accurate at one point in time but diagnostic results may lose applicability, accuracy, or relevance as user characteristics or user activities change (e.g., as a user loses weight, alters activity habits, stops smoking, reduces blood glucose level, etc.).

A desire thus exists for informing and monitoring blood flow simulations with user-specific activity data. The foregoing general description and the following detailed description are exemplary and explanatory only and are not restrictive of the disclosure. The present disclosure pertains to, for example, $FFR_{CT}$, PCI and CABG planning, perfusion modeling, mobile viewers, and anything related to hyperemic simulation, planning, and long-term follow-up, according to one embodiment.

SUMMARY

According to certain aspects of the present disclosure, systems and methods are disclosed for informing and monitoring blood flow calculations with user-specific activity data, including sensor data.

One method includes receiving or accessing a user-specific anatomical model and a first set of physiological characteristics of a user; calculating a first value of a blood flow metric of the user based on the user-specific anatomical model and the first set of physiological characteristics; receiving or calculating a second set of physiological characteristics of the user by accessing or receiving sensor data of the user's blood flow and/or sensor data of the user's physiological characteristics; and calculating second value of the blood flow metric of the user based on the user-specific anatomical model and the second set of physiological characteristics of the user.

In accordance with another embodiment, a system for calculating blood flow metrics using sensor data comprises: a data storage device storing instructions for calculating blood flow metrics using sensor data; and a processor configured for: receiving or accessing a user-specific anatomical model and a first set of physiological characteristics of a user; calculating a first value of a blood flow metric of the user based on the user-specific anatomical model and the first set of physiological characteristics; receiving or calculating a second set of physiological characteristics of the user by accessing or receiving sensor data of the user's blood flow and/or sensor data of the user's physiological characteristics; and calculating second value of the blood flow metric of the user based on the user-specific anatomical model and the second set of physiological characteristics of the user.

In accordance with another embodiment, a non-transitory computer readable medium for use on a computer system containing computer-executable programming instructions for performing a method of calculating blood flow metrics using sensor data, the method comprising: receiving or accessing a user-specific anatomical model and a first set of physiological characteristics of a user; calculating a first value of a blood flow metric of the user based on the user-specific anatomical model and the first set of physiological characteristics; receiving or calculating a second set of physiological characteristics of the user by accessing or receiving sensor data of the user's blood flow and/or sensor data of the user's physiological characteristics; and calculating second value of the blood flow metric of the user based on the user-specific anatomical model and the second set of physiological characteristics of the user.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

Figure 1:
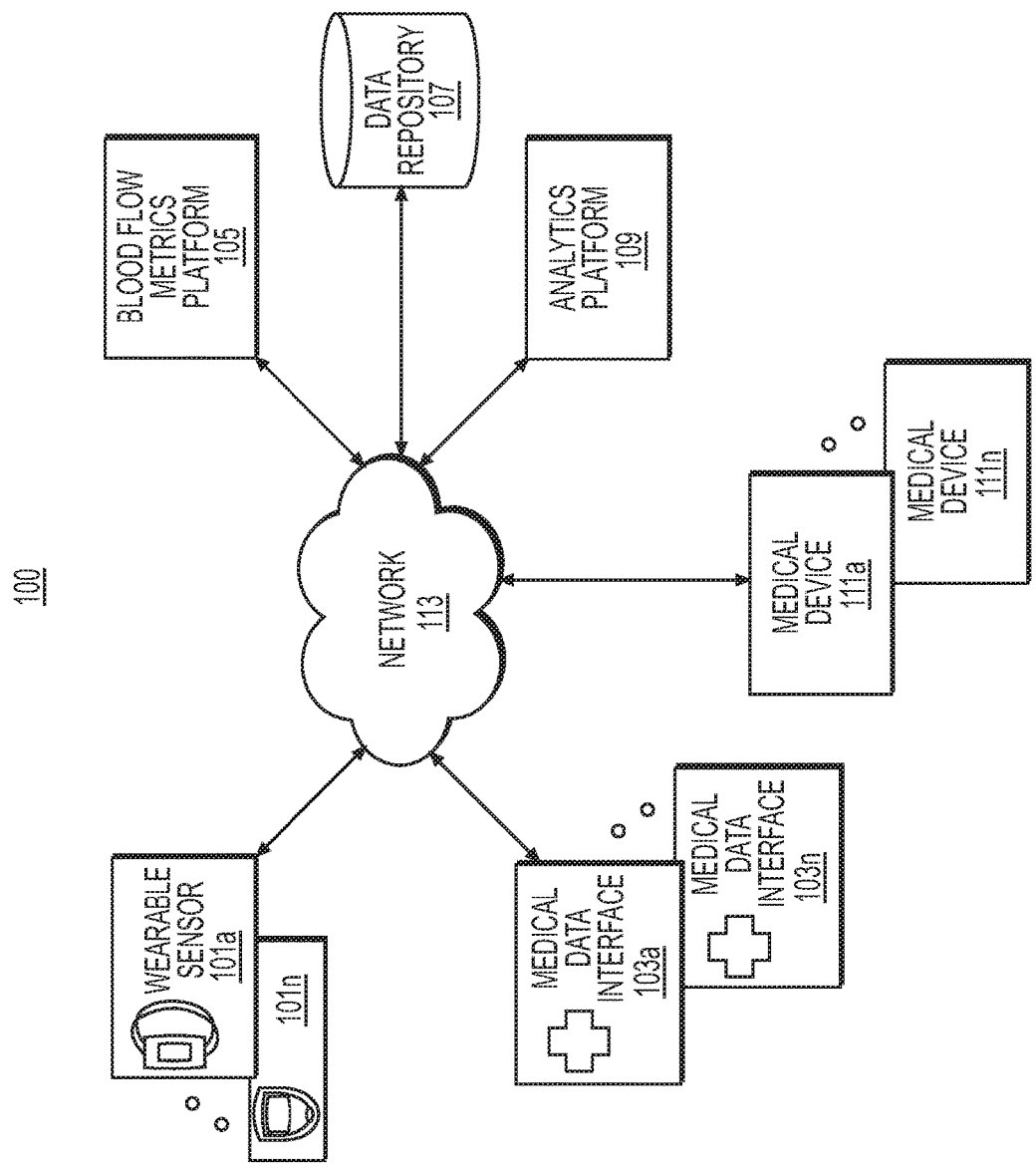
FIG. 1 is block diagram of an exemplary blood flow monitoring system using user-specific activity data, according to an exemplary embodiment of the present disclosure.

As used herein, the term "exemplary" is used in the sense of "example," rather than "ideal." In addition, the terms "first," "second," and the like, herein do not denote any order, quantity, or importance, but rather are used to distinguish one concept or structure from another. Moreover, the terms "a" and "an" herein do not denote a limitation of quantity, but rather denote the presence of one or more of the referenced items. For the purposes of the disclosure, "patient" and "user" may refer to any individual or person for whom diagnosis or treatment analysis (e.g., data analysis) is being performed, or any individual or person associated with the diagnosis or treatment analysis of one or more individuals. Furthermore, "health state" or "state of health" may refer to a medical condition, comprising a collection of symptoms, characteristics, triggers, causes, or indicators associated with the medical condition.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Embodiments of this disclosure include systems and methods for capturing, analyzing, and using user-specific activity data to inform physiologic blood flow simulations, and to monitor and predict future events based on blood flow simulation and activity data.

Coronary artery disease may cause blood vessels providing blood to the heart to develop lesions, e.g., a stenosis. As a result, blood flow to the heart may be restricted. A user suffering from coronary artery disease may experience chest pain, (e.g., chronic stable angina) during physical exertion or unstable angina when the user is at rest. A more severe manifestation of disease may lead to myocardial infarction, or heart attack. A desire exists to provide more accurate data relating to coronary lesions, such data including information on each lesion's size, shape, location, functional significance (e.g., whether the lesion impacts blood flow), etc. Users suffering from chest pain and/or exhibiting symptoms of coronary artery disease may be subjected to one or more tests (e.g., tests based on medical imaging) that may provide some indirect evidence relating to coronary lesions. Many other areas of cardiology may have similar needs for diagnosing atherosclerosis, congenital anomalies, or other vascular diseases, e.g., disease of the peripheral, cerebral, renal, and pulmonary vascular systems.

Common cardiovascular imaging techniques include CT, SPECT, MR, and echocardiography. In addition to the use of medical imaging for noninvasive coronary evaluation, coronary evaluations may include electrocardiograms, biomarker evaluation from blood tests, and treadmill exercise tests. These noninvasive tests, however, may not provide a direct assessment of coronary lesions or assess blood flow rates through individual vessels that may or may not require treatment. The noninvasive tests may provide indirect evidence of coronary lesions by looking for changes in electrical activity of the heart (e.g., using electrocardiography (ECG)), motion of the myocardium (e.g., using stress echocardiography), overall perfusion of the myocardium (e.g., using PET or SPECT), or metabolic changes (e.g., using biomarkers).

Anatomic data may be obtained noninvasively using coronary computed tomographic angiography (CCTA). CCTA may be used for imaging of users with chest pain and involves using CT technology to image the heart and the coronary arteries following an intravenous infusion of a contrast agent. However, CCTA may not provide direct information on the functional significance of coronary lesions, e.g., whether the lesions affect blood flow. In addition, CCTA, used alone, may be neither used to predict changes in coronary blood flow, pressure, or myocardial perfusion under various physiological states (e.g., exercise, rest, hyperemia, etc.), nor used to predict outcomes of interventions.

Thus, users may undergo an invasive test, e.g., diagnostic cardiac catheterization, to visualize coronary lesions. Diagnostic cardiac catheterization may include performing conventional coronary angiography (CCA) to gather anatomic data on coronary lesions by providing a doctor with an image of the size and shape of the arteries. CCA, however, may not provide data for assessing the functional significance of coronary lesions. For example, a doctor may not be able to diagnose whether a coronary lesion is harmful without determining whether the lesion is functionally significant. Thus, CCA has led to a procedure referred to as an "oculostenotic reflex," in which interventional cardiologists may insert a stent for every lesion found with CCA regardless of whether the lesion is functionally significant. As a result, CCA may lead to unnecessary operations on the user, which may pose added risks to users and may result in unnecessary heath care costs for users.

During diagnostic cardiac catheterization, the functional significance of a coronary lesion may be assessed invasively by measuring the fractional flow reserve (FFR) of an observed lesion. FFR may be defined as the ratio of the mean blood pressure downstream of a lesion divided by the mean blood pressure upstream from the lesion, e.g., the aortic pressure, under conditions of increased coronary blood flow, e.g., when induced by intravenous administration of adenosine. Blood pressures may be measured by inserting a pressure wire into the user. Thus, the decision to treat a lesion based on the determined FFR may be made after the initial cost and risk of diagnostic cardiac catheterization has already been incurred. Even FFR may not provide the ability to predict what may happen to the specific user in the near-term or far-term future if a treatment is made.

To fill the gaps left by each of the pure medical imaging and invasive procedures described above, simulation and modeling technology based on user-specific imaging data has been developed. For example, various simulation, modeling, and computational techniques include, but are not limited to: computational mechanics, computational fluid dynamics (CFD), numerical simulation, multi-scale modeling, Monte Carlo simulation, machine learning, artificial intelligence, and various other computational methods to solve mathematical models. These techniques may provide information about biomechanics, fluid mechanics, changes to anatomy and physiology over time, electrophysiology, stresses and strains on tissue, organ function, and neurologic function, among others. This information may be provided at the time of the imaging study and/or shown as predicted changes over time, either as a result of medical procedures or as a result of the passage of time and progression of disease.

One illustrative application of computational simulation and modeling may include modeling vascular blood flow from non-invasive imaging data, including assessing the effect of various medical, interventional, or surgical treatments. In particular, methods have been developed for noninvasively assessing coronary anatomy, myocardial perfusion, and coronary artery flow, to reduce the above disadvantages of invasive FFR measurements. Specifically, CFD simulations have been successfully used to predict spatial and temporal variations of flow rate and pressure of blood in arteries, including FFR. Exemplary methods for performing and using noninvasive blood flow modeling is described in U.S. Pat. No. 8,386,188 issued Mar. 26, 2013, U.S. Pat. No. 8,321,150 issued Nov. 27, 2012, U.S. Pat. No. 8,315,814 issued Nov. 20, 2012, U.S. Pat. No. 8,315,813 issued Nov. 20, 2012, U.S. Pat. No. 8,315,812 issued Nov. 20, 2012, U.S. Pat. No. 8,311,750 issued Nov. 13, 2012, U.S. Pat. No. 8,311,748 issued Nov. 13, 2012, U.S. Pat. No. 8,311,747 issued Nov. 13, 2012, and U.S. Pat. No. 8,157,742 issued Apr. 17, 2012, all of which are hereby incorporated by reference in their entireties.

Such methods and systems benefit cardiologists who diagnose and plan treatments for users with suspected coronary artery disease, and predict coronary artery flow and myocardial perfusion under conditions that cannot be directly measured in a catheterization lab (e.g., exercise). Such systems and methods further permit prediction of outcomes of medical, interventional, and surgical treatments on coronary artery blood flow and myocardial perfusion.

Current stress testing procedures (e.g., FFR or perfusion imaging) often use pharmacologically-induced hyperemia to simulate maximum exercise of a user. Alternatively, stress-treadmill tests may utilize echocardiography or ECG measurements while a user exercises on a treadmill, simulating their real world activity. Both methods, treadmill testing and pharmacologically-induced hyperemia, may be limited in their attempt to simulate the real-world experience of a user and the symptoms of ischemia they may experience. A user may have a positive FFR result while describing his/her experience as asymptomatic for ischemia; this may be because a user may limit his/her activity level to reduce symptoms, thereby restricting his/her lifestyle. Alternatively, a user may report symptoms that a treadmill test cannot replicate in a lab. For example, a user may experience symptoms while walking up subway stairs in the cold weather. A desire exists for a test to better couple the real-world activity of a user with measurements of their blood flow, pressure, and other physiologic metrics that can be used to diagnose cardiovascular disease.

Additionally, after a decision is made on how to treat a user (e.g., medical therapy with monitoring, percutaneous intervention like stenting a stenosis, or surgical revascularization like coronary artery bypass), there is a desire to understand how that user's condition may progress over time. A user on medical management may successfully reduce their symptoms over time with proper exercise and medical treatment. Alternatively, the user's symptoms may still exist and become worse over time, either due to disease progression or activity and lifestyle changes. A desire exists to predict and monitor the relationship of user activity to symptoms and disease progression over time.

This disclosure includes at least four exemplary embodiments, which may be implemented individually, or in combination:

1) A system and method for gathering user-specific activity data prior to a cardiovascular analysis for the purpose of informing the analysis and preparing the user for any procedures related to the analysis.

2) A system and method for tracking and monitoring user activity data after a cardiovascular analysis for the purpose of informing the user and physician of changes to the user's condition.

3) A system and method for obtaining a CT-derived treadmill or exercise test with lesion-specific functional data, which may provide a level of detail not currently possible with CT-alone or with current stress treadmill tests.

4) A system and method for predicting long-term changes to the user's condition based on their activity data.

In the first embodiment, a blood flow monitoring system and method are described to capture user-specific activity data and analyze the data to compute blood flow metrics. Alternately or in addition, the user-specific activity data may be used to perform user-specific blood flow simulations. In some cases, blood flow metrics may relate to cardiovascular activity of the user. Software may be installed on a hardware device capable of detecting activity or physiologic data with sensors, including but not limited to accelerometers, gyroscopes, altimeter pressure sensors, heart rate sensors, blood pressure sensors, blood testing sensors, image sensors, GPS sensors, etc. Devices that contain such sensors may include handheld devices, e.g., phones, tablets, or glucose monitors; and wearable devices, e.g., watches, bracelets, rings, pendants, pins, monitors, etc. Prior to a cardiovascular analysis, medical image data of the user's anatomy may be acquired. Before an exam is scheduled, software may be installed on the user's existing device. Alternatively or in addition, the user may be given a device with preinstalled software to wear or use prior to their imaging exam.

In one embodiment, a blood flow monitoring system may include a user interface to accept input and display output to the user. The software may prompt a set-up by a user (e.g., the user or a medical professional) to input data about the user, e.g., their height, weight, age, sex, scheduled exam date, etc. This data may be used by the software to determine blood flow metrics from the activity data. The display may allow the software to communicate notifications, images, or other information to the user.

In one embodiment, the blood flow monitoring system may further capture sensor data at pre-specified intervals (e.g., every 10 ms, every 5 seconds, every hour, etc.). The sensor data may be compiled into a data structure representing changes in data over time. In an exemplary embodiment, accelerometer data related to movement, barometric elevation data, heart rate data, and gyroscopic data may be tracked over time and stored in a database. The data may be stored on the device and/or transmitted remotely to another computer system for analysis. Remote transfer may occur by any means, e.g., wireless network, cellular data network, or other near or far range electromagnetic frequencies, etc.

The blood flow monitoring system, either on the device or remotely, may analyze the activity data to derive cardiovascular or physiological metrics. The data may be analyzed in real-time as it is acquired, at set time intervals using multiple data-points together, or all at once after all relevant data has been acquired. Metrics may include: cardiac output, work and energy output of the user, microvascular resistance, level of hyperemic response, etc. These blood flow metrics may not be directly measured by the device's sensors. The metrics may be derived from the user's activity data (as provided by one or more sensors).

Once the blood flow metrics are defined, the blood flow monitoring system may determine at least one of a multitude of metrics related to the user's activity, e.g., percentage of time experiencing ischemia, specific times the user may have experienced symptoms, activity level at which point the user may experience symptoms, comparison of maximum hyperemic response from activity versus maximal medically induced hyperemia, simulated treadmill test, analyze events correlated with activity data, using machine learning (e.g., without computational fluid dynamics) to predict events, etc.

Once a user is using the activity-tracking device of the blood flow monitoring system, the blood flow monitoring system may prompt the activity-tracking device to remind or alert the user to perform various activities. The blood flow monitoring system may further monitor the user and confirm that the user performs the activities. For example, the device may remind a user to take medication at a certain time or not eat for a specified amount of time before an imaging exam. The device may further detect whether a user follows the instructions of a reminder (e.g., detecting changes to blood flow or blood sugar in response to medications or food consumption). The blood flow monitoring system may provide a notification through messaging, images, alerts, or physical responses (e.g., vibrations or other haptic signals). The system may also prompt the user to confirm they followed certain instructions from their physician or medical professional.

Additionally, the blood flow monitoring system may receive and use user input. For example, if a user feels chest pain upon performing a strenuous activity, the user may record that event of chest pain via the blood flow monitoring system. As another example, the blood flow monitoring system may prompt a user to describe his/her symptoms or health conditions. The blood flow monitoring system may record and store event type and time. In one case, the blood flow monitoring system may designate various activities or activity levels (e.g., light activity, strenuous activity, etc.), and the blood flow monitoring system may associate detected or user-reported events with detected activities/ activity levels. The blood flow monitoring system may also correlate medical events/symptoms with activity data recorded before, during, and after the event. As previously discussed, the activity data may be provided by the sensor data and/or user input.

In the present disclosure, an initial personalized simulation may benefit from being linked to actual user activities (e.g., exercise ability, frequency, real-world activity, peak physiologic conditions vs. medically induced physiologic conditions, etc.) to provide an initial simulation that may be representative of the user's real-world physiologic condition. By extension, a simulation system may be initially informed by user-specific activity, and diagnostic simulations may be recalculated or regularly updated as the user changes. For example, a user or doctor could be alerted if the calculations revealed that the user may have exhibited dangerous or concerning calculated metrics/characteristics. In another example, medication may be automatically dispensed to the user if the calculations indicate a physical condition that may be dangerous for the user. While many of the embodiments described refer to blood flow simulations and blood flow calculations, the disclosed systems and methods may apply to any diagnostic simulation and metric.

Alternately or in addition, calculations of metrics may also benefit from a user inputting information, e.g., symptoms. In one embodiment, user input may be correlated with information gathered with a wearable, medical, and/or home health device and used to refine a simulation. For example, users may define symptoms correlated with various physical activities. Such symptoms may produce measureable physiologic signals, which may be used to refine the simulation to better predict the relationship between that user's blood flow characteristics and their state of health. For example, user input and sensor data from a heart beat monitor may be used to better predict the relationship between the user's blood flow and level of ischemia. The relationship between the blood flow and level of ischemia may then be user-specific and continually updated, rather than based on correlations from empirical data or assumptions from earlier studies.

In other words, a user blood flow simulation may be updated continually with data provided by a wearable, medical, or home health device associated with a user or with data directly input by a user. Alternately or in addition, blood flow models providing the basis for the user blood flow simulation may be continually updated or refined using the user data (e.g., collected data, measured data, data input by the user, etc.) and/or data from other users and wearable, medical, or home health devices associated with each of those other users. For instance, the present disclosure may include methods for updating boundary conditions, a user-specific anatomic model, or initial conditions used to calculate blood flow metrics (and a user's medical condition). The updates may be derived from user input and sensor data. For example, a user displaying symptoms of an exercise physiological state (e.g., elevated heart rate) during moderate activity (e.g., slow walking), may trigger the disclosed system and method to infer a modification to an anatomic model associated with the user. One such modification may include a narrowing of vasculature. Vascular narrowing may then be reflected in a geometrical change to the anatomical model associated with the user, as well as a boundary condition model corresponding to the vascular narrowing, where both the updated anatomical model and updated boundary condition model may be used to calculate a value of a blood flow metric for the user. The calculated value of the blood flow metric may indicate the user's medical condition.

Alternately or in addition, one embodiment may include defining groups of users (e.g., by age, demographics, exercise levels/regimen, medical history, employer, health care provider, health care plan, insurance provider, wearables used, etc.). Blood flow models may be trained specifically within each of the groups of users. For instance, a first group of users of ages 18-35 may have a selected blood flow model specific to that first user group and a second group of users ages 36-50 may have a selected blood flow model specific to that second user group. As described above, each blood flow model may include user-specific computational model(s) (e.g., with defined boundary conditions), user-specific anatomical model(s), and/or user-specific blood flow models trained from data related to various individuals (e.g., via machine learning.) Each of these blood flow models may be updated and refined continually using data from wearable, medical, or home health devices associated with users of that user group.

Baselines or thresholds for healthy individuals may further be refined using such sensor data. For example, aggregated sensor data may indicate different threshold values or baselines to use for each user group. For instance, an average resting heart rate for adults at rest may generally be 60-100 beats per minute. The average resting heart rate for athletes is about 40-60 beats per minute. Aggregated sensor data may be used to further estimate average resting heart rate for adults of certain age ranges (e.g., ages 18-35 or ages 36-50), adults that engage in certain exercises, and/or adults that maintain certain diets. This data may further inform blood flow models by determining whether a given user may have a medical condition. In this way, sensor data may be used to increase accuracy of blood flow simulations and predictions.

An alternative or additional grouping may involve users of various insurance providers. For example, users of a first insurance provider may correspond to one blood flow model and have that blood flow model supplemented by wearable device data associated with users covered by that first insurance provider, while users of a second insurance provider may have their blood flow simulations based on blood flow models supplemented by wearable device data from users covered by that second insurance provider. In one scenario, the first insurance provider may provide or encourage their customers/users to use one set of wearable devices, while the second insurance provider may encourage their customers to use a different set of wearable devices. In such a case, resultant blood flow model(s) could develop differently between the various groups.

In addition, groups may be defined based on devices used to collect user data. For example, analysis of simulation data from such groups may permit indications as to which wearable devices provide or collect the most pertinent data for various blood flow simulations. For example, for a given blood flow simulation, heart rate monitors may produce better blood flow models than blood pressure cuffs. Alternately or in addition, blood flow models may eventually indicate that one wearable, medical, or home health device is superior to another in providing data for blood flow simulations. For example, one brand's heart rate monitor may provide data that results in a more accurate blood flow model/simulation than another brand's heart rate monitor.

A similar use case scenario may occur for a social group, e.g., a gym membership or employer/workplace, where users/consumers that are part of the social group may have their data tracked by a wearable device whose data may continually modify a blood flow model. In the present disclosure, that wearable data-based blood flow model may be used to evaluate the health/blood flow of the users/consumers that are members of the social group, as well as users/consumers that are not part of the social group.

Exemplary systems and methods may also include comparing blood flow models of various user groups, e.g., to find trends or infer heath conditions between groups. User blood flow simulation information between groups may also be compared, e.g., to set insurance premiums or map risk for consumers/users of various ages, demographics, medical histories, professions, etc. Using wearable data in such analyses may entail, for example, insurance premiums that could be fluid or change in shorter time intervals, based on a consumer/user's exercise level. Risk mapping may also be more refined when using sensor data to tailor blood flow models and simulations. For example, one embodiment may include a jogging club where members may visualize their risk of heart failure, during their jog or over the course of a selected period of time. Local governments, schools, or other groups could also evaluate whether various health initiatives had an impact on the health of their constituency via blood flow simulations based on data from wearable, medical, or home health devices.

One exemplary embodiment may include producing visualizations comparing various users of a user group and/or comparing a user to his or her entire user group. For example, a visualization may include the option for athlete "A" to compare his or her risk to athlete "B's" risk. For instance, athlete A and athlete B may have a target low risk level that they are working towards and the wearable data-based visualization may provide accountability and encouragement between the two athletes to reach that risk level. An exemplary comparison of a user against an entire user group may include a user paying a given insurance premium, where the premium may be set according to a user disease risk level. The user may compare his or her wearable data-based blood flow simulation calculations to blood flow simulation measurements of the other users in his or her insurance program. In another embodiment, an insurance premium may increase if the user's risk level exceeds a predetermined risk level. Having blood flow simulation data based on data from a wearable device may mean that the user can see how close he or she is getting to the predetermined risk level.

In one embodiment, the disclosed systems and methods may provide a report including a projected outcome or timing for a change in health state, should the user's input (via the wearable device) proceed a certain way. For example, a user may be at a first health state, given his or her current exercise regimen. The report may include a projected health state for a given amount of time, should the user continue his or her current exercise regimen. Alternately, or in addition, the report may provide a projected health state should the user increase or decrease his or her current exercise regimen. The projected health state may be determined based on blood flow simulations or models updated continually using user-generated sensor data and user input, both from a single user and groups of users.

All embodiments described above with respect to data from wearable devices, may also be applied to medical or home health devices.

Figure 2:
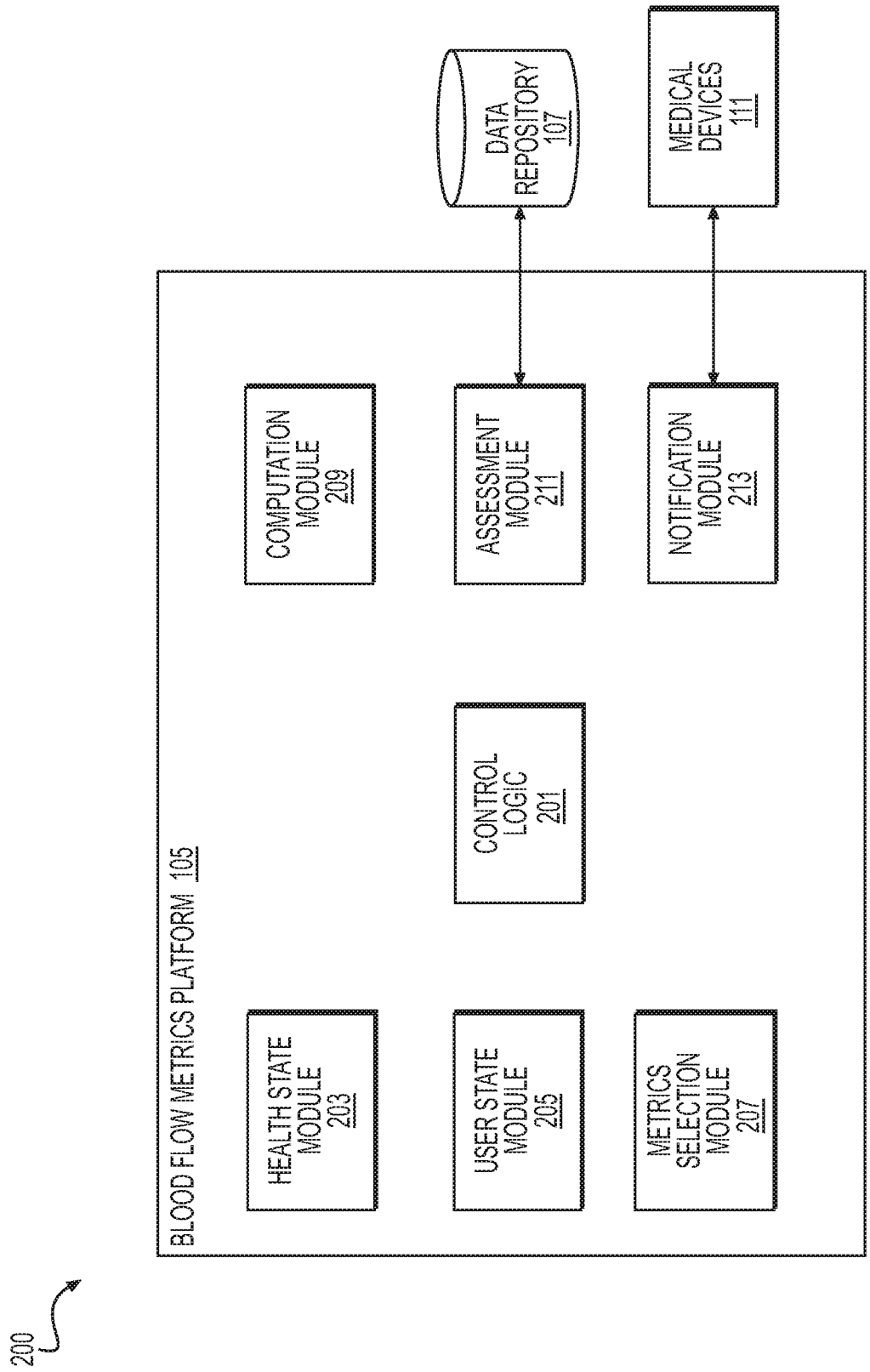
FIG. 2 is a block diagram of an exemplary blood flow metrics platform for computing blood flow based on user-specific activity data, according to an exemplary embodiment of the present disclosure.
Figure 3:
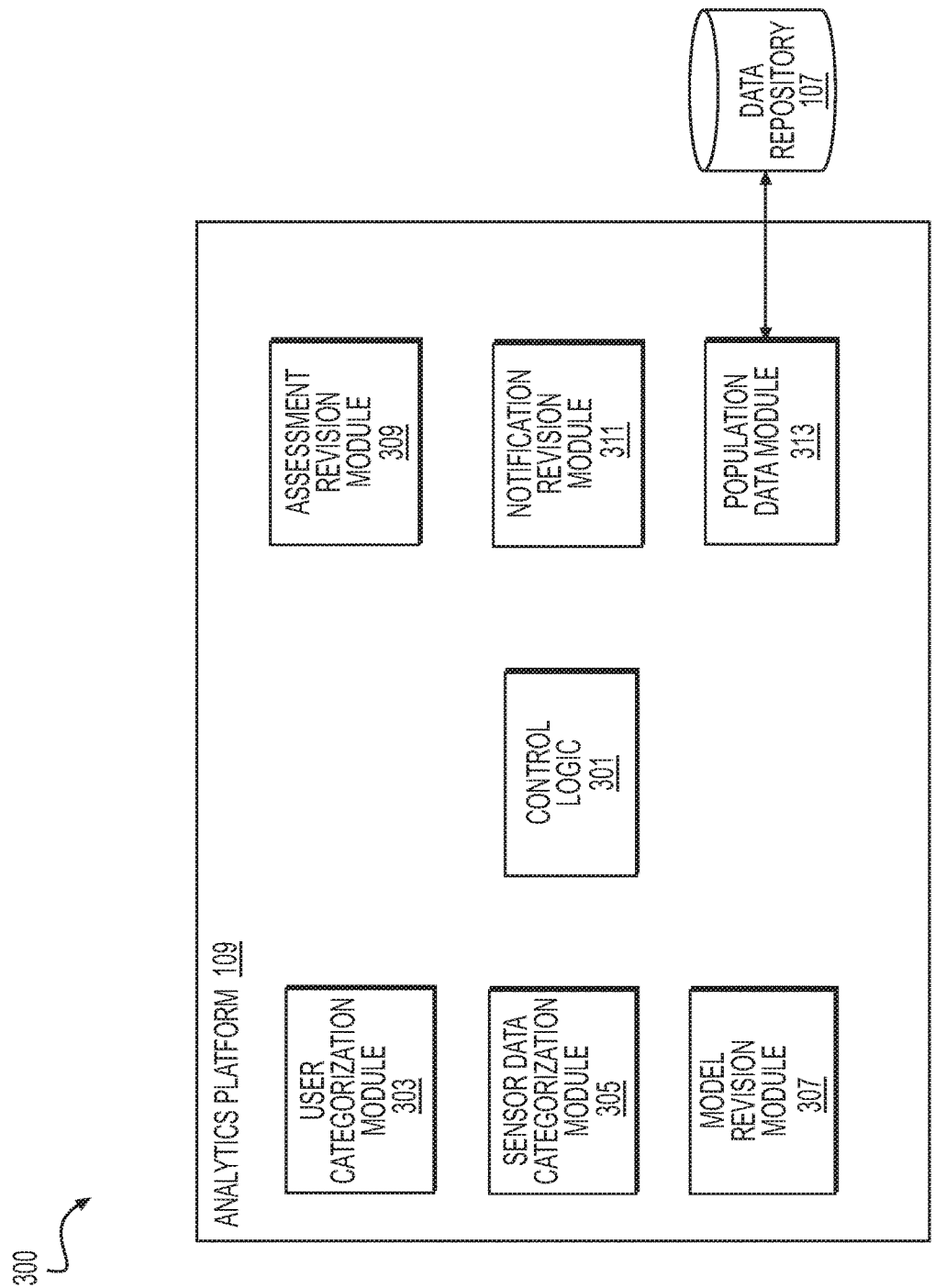
FIG. 3 is a block diagram of an exemplary analytics platform that uses user-specific activity data to enhance models and assumptions employed in blood flow computations, according to an exemplary embodiment of the present disclosure.

FIG. 1 is a general embodiment of a system which uses sensor data to calculate blood flow metrics for a particular user. The sensor data may include activity data of the user, for instance, sensor data indicating the user's physiological state. The calculated blood flow metrics may indicate the user's state of health. The system may thus include sensors (e.g., from wearable devices), user medical data (e.g., medical history or anatomical images/measurements), blood flow computation capabilities, and capabilities to produce outputs associated with the computed blood flow and user health (e.g., functions for predicting the user's future health progression, reporting the user's health, and/or dispensing medication). FIG. 2 is a block diagram of an exemplary platform for computing blood flow from sensor data. FIG. 3 is a block diagram of an exemplary analytics platform for tailoring assumptions and models used in those blood flow computations. In particular, the exemplary analytics platform of FIG. 3 may update the assumptions and models based on user sensor data and past blood flow computations.

Figure 4:
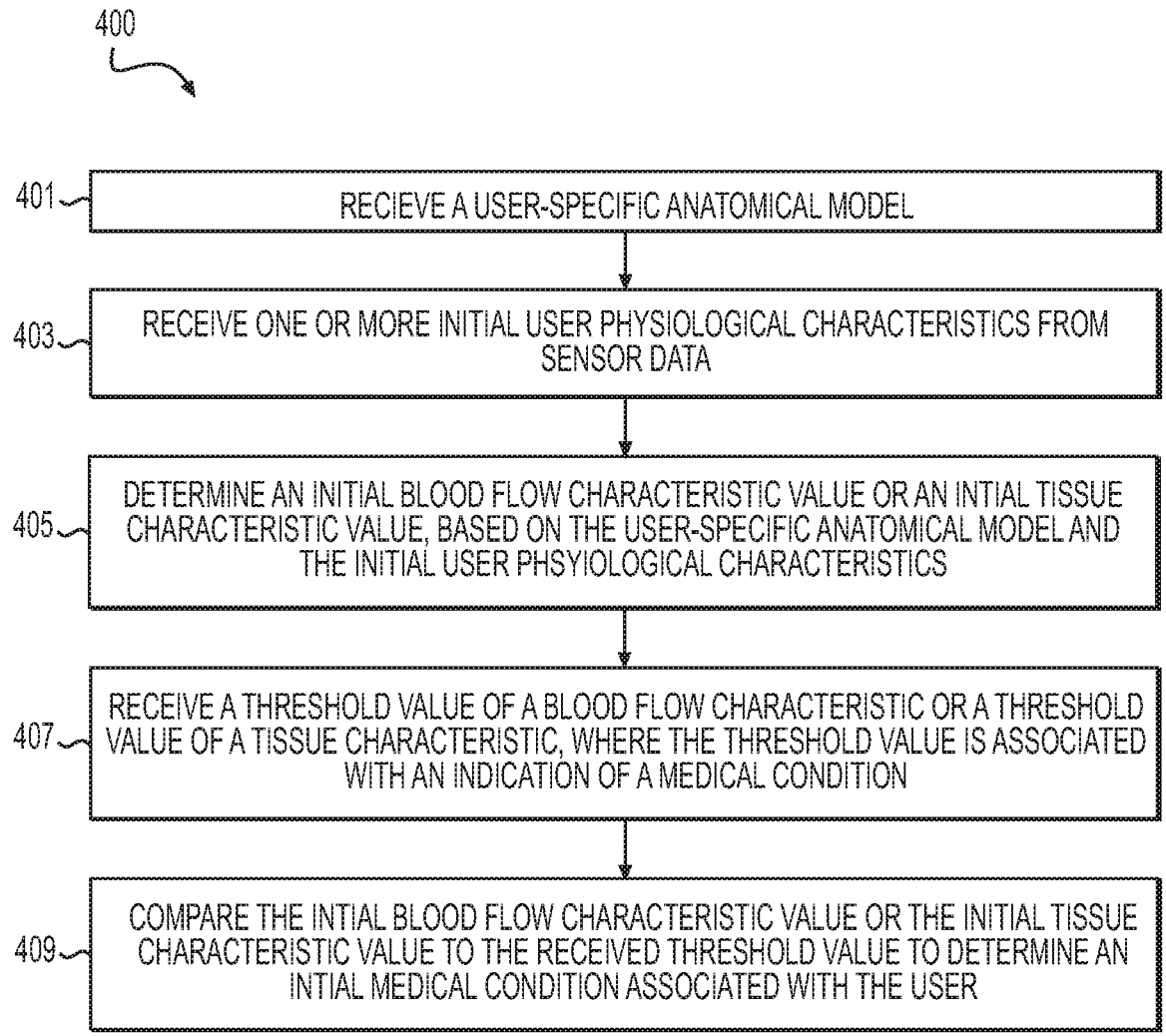
FIG. 4 is a flow diagram of an exemplary method of initializing a blood flow model of a user for the blood flow computations based on user-specific activity data, according to an exemplary embodiment of the present disclosure.
Figure 5:
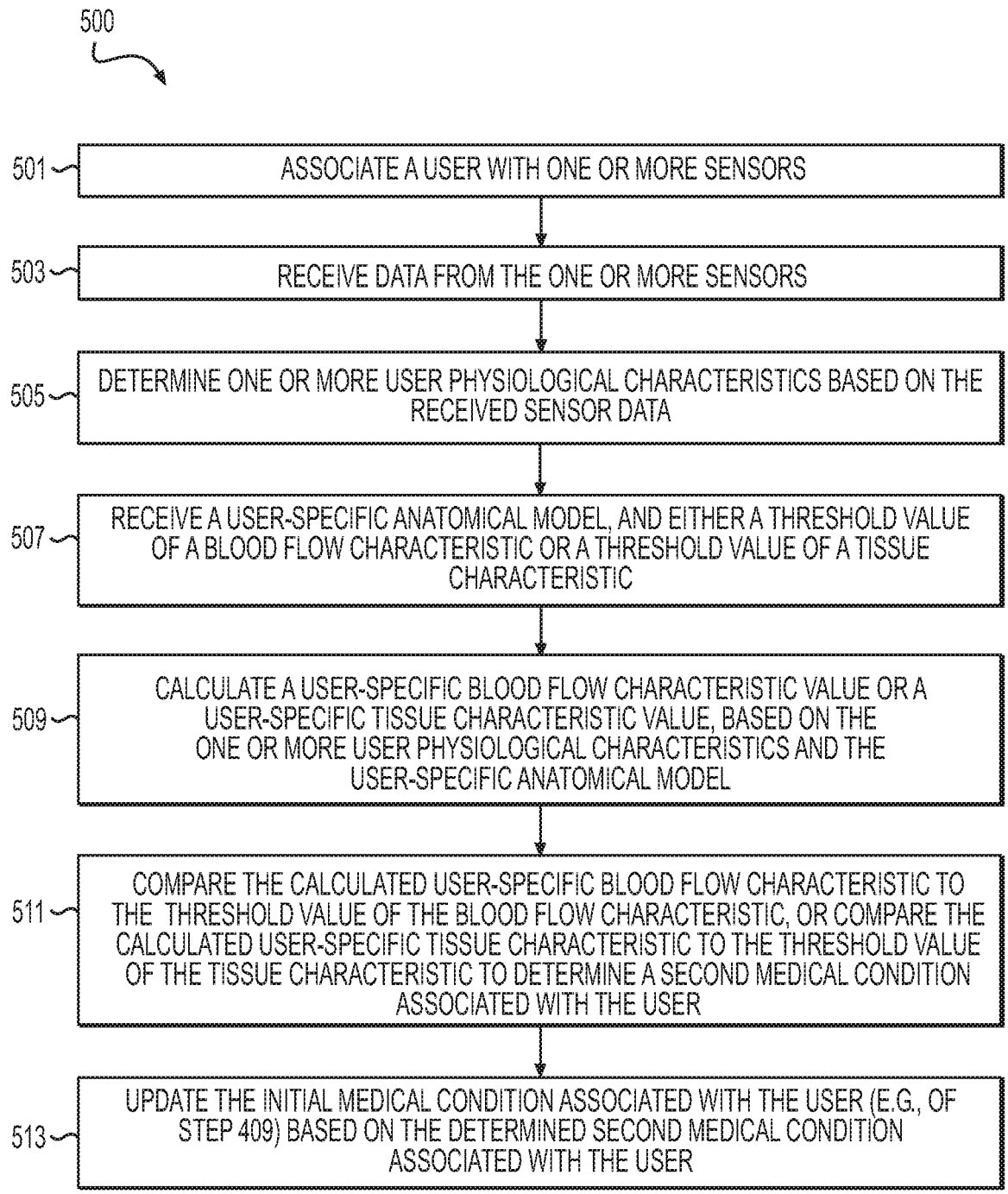
FIG. 5 is a flow diagram of determining a user's state of health on a real-time basis using user-specific activity data, according to an exemplary embodiment of the present disclosure.

FIGS. 4 and 5 depict flow diagrams of processes for monitoring and calculating a user's blood flow metrics using user-specific activity data. In particular, FIG. 4 is a process of initializing a user's blood flow computations and determining a user's initial state of health. FIG. 5 includes a process of continually updating the user's blood flow computations based on sensor data, and continually updating an understanding of the user's state of health.

FIG. 1 depicts a block diagram of an exemplary blood flow monitoring system 100 for monitoring and simulating a user's blood flow using ongoing sensor data, according to an exemplary embodiment. Blood flow monitoring system 100 may receive sensor data from wearables or other consumer devices and detect a user's state of health based on the sensor data. Blood flow monitoring system 100 may also alert or prompt action of a medical professional or device, depending on the detected state of health. For example, blood flow monitoring system 100 may cause a medical device to dispense medication if metrics calculated from a user's blood flow simulation indicate that the user may be in need of medication. Blood flow monitoring system 100 may also alert a medical professional if a user's blood flow simulation outputs blood flow metrics that fall within a predetermined range for the medical professional to be informed. Further, blood flow monitoring system 100 may provide a report of a user's ongoing activity and blood flow simulation metrics, for example, prior to a medical exam and/or over a range of past, present, and future times.

Blood flow monitoring system 100 may also refine its simulations based on the sensor data. For example, blood flow monitoring system 100 may use sensor data and real-time input on a user's activity to update physiological assumptions underlying blood flow simulations. Blood flow monitoring system 100 may further use sensor data to determine user-specific calculations. For example, physiological assumptions that apply to one person may not apply to another person. Two people running at the same speed may experience different heart rates and therefore express different blood flow conditions. Blood flow monitoring system 100 may use real-time input to provide blood flow metrics that are computed with user-specific physiological assumptions, meaning models of blood flow may be based on assumptions unique to each individual user, on a real-time basis.

In one embodiment, blood flow monitoring system 100 may be comprised of various components including one or more sensors 101a-101n (e.g., sensors 101), one or more medical data interfaces 103a-103n (e.g., medical data interfaces 103), a blood flow metrics platform 105, a data repository 107, an analytics platform 109, one or more medical devices 111a-111n (e.g., medical devices 111), and a network 113.

In one embodiment, sensors 101 may receive ongoing user activity data. Sensors 101 may include any consumer devices, including heart rate monitors, Holter monitors, pacemakers, or other heart rhythm monitoring devices, phones, smart watches, blood pressure cuffs, accelerometers (e.g., in a smart phone or watch), exercise equipment (e.g., treadmills, stationary bikes, ellipticals, etc.), bathroom scales, smart toilets, sleep monitors, glucose monitors, insulin pumps, smartphone applications (e.g., apps logging sleep, exercise, diet, food intake, fertility cycles, etc.), etc. In one embodiment, medical data interfaces 103 may receive user health data, e.g., data generated by medical professionals or facilities. User health data may include medical reports, images, anatomic models (e.g., CT scans), etc.

In one embodiment, blood flow metrics platform 105 may compute blood flow metrics of a user, based on data received from sensors 101 and/or medical data interfaces 103. In one embodiment, blood flow metrics platform 105 may receive a user-specific anatomical model from the medical data interfaces 103. The user-specific anatomical model may include an anatomical model of a portion of the user's vasculature and/or tissue. Alternately or in addition, the user-specific anatomical model may include a model of the user's entire circulatory system or tissues. In one embodiment, the data from the sensors 101 may provide data indicating a physiological state of the user. Blood flow metrics platform 105 may calculate blood flow characteristic(s) or tissue characteristic(s) of the user using the user-specific anatomical model from the medical data interfaces 103 and using physiological characteristics from the sensors 101.

In one embodiment, blood flow metrics platform 105 may calculate the user-specific blood flow characteristic(s) or tissue characteristic(s) by simulating blood flow through the received user-specific anatomical model, where the simulation is performed taking into account the physiological characteristics provided by the sensor data. For example, the geometry of vasculature of the anatomical model and/or boundary conditions of the flow simulation may be adjusted according to the received physiological characteristics. Exemplary systems and methods for adjusting blood flow simulations based on physiologic conditions are described in U.S. Pat. No. 9,202,010 issued Dec. 1, 2015, the entire disclosure of which is hereby incorporated in reference in its entirety.

In one embodiment, data repository 107 may receive and store computed blood flow metrics. For example, data repository 107 may provide longitudinal data for a specific user, or for a group of users. In one embodiment, analytics platform 109 may update computations of the blood flow metrics platform 105 and/or provide aggregate user data. Updating computations may entail forming associations among groupings of users. For example, groupings of users may include grouping users by wearable type/sensor type, demographics, insurance policy, age, health goals, user self-selected groupings (e.g., a gym membership or running club), etc. Alternately or in addition, analytics platform 109 may determine one or more recommended treatment regimens, therapy tasks, reports, follow-up tests/analyses, etc.

The blood flow metrics platform 105, data repository 107, and/or analytics platform 109 may further provide predictions of a user's health state, e.g., at various physiological states, at different points of time, or if a user's sensor data reflects certain physiological states or user health practices. For example, the blood flow metrics platform 105 may compute a value of a user's blood flow metric at a physiological state that the user is not currently experiencing. In one such case, a user may be at a resting physiological state and the blood flow metrics platform 105 may estimate a value of a user's blood flow metric for when the user is at an exercise state, based on the blood flow simulations and sensor data received from the user from the user's previous exercise sessions. The blood flow metrics platform 105 may also predict a value of a user's blood flow metric, if a user engages in certain practices. For example, the blood flow metrics platform 105 may calculate a value of a user's blood flow metric (e.g., FFR), if the user exercises daily for a month, or for a year. The blood flow metrics platform 105 may also evaluate a user's health or progress against other users within a group. Such groups may be voluntarily defined by the user (e.g., a health club or a mobile app that the user installs). Alternately or in addition, such groups may be dictated by factors outside the control of a given user. For example, groupings may also be defined by hospitals, insurance companies, manufacturers of wearable devices or sensors, etc. Such calculations of the blood flow metrics platform 105 may be supplemented with stored data or analyses provided by the data repository 107 and/or analytics platform 109.

In one embodiment, medical devices 111 may dispense medication or initiate an alert, based on data of the blood flow metrics platform 105 and/or analytics platform 109. The alert may be provided to the user, individual(s) associated with the user (e.g., family members or neighbor(s)), and/or a medical professional. For example, if a user is detected to possibly be experiencing a stroke, medical devices 111 may provide an alarm to the user's doctor, a local clinic, or the user's family. Medical devices 111 may further request input from the user, prompting the user to respond and confirm/deny symptoms that the user may be experiencing. The alarm or alert may take any form, e.g., a visual indicator on a user interface, an auditory signal, a haptic trigger, etc.

In one embodiment, medical devices 111 may include a portal, where a user or health care professional may track or monitor a user's state of health. In one embodiment, the medical devices 111 may further provide recommended treatment regimens, therapy tasks, reports, follow-up tests/ analyses, etc. The recommended treatment regimens, therapy, reports, or follow-up tests/analyses may be user-specific, e.g., based on metrics calculated from user-specific blood flow simulations and the user's sensor data or input, and/or based on prior treatments/tests/analyses that the user has undergone.

In one embodiment, medical devices 111 may further include interface(s) and/or portal(s) where various users may access blood flow metrics data or logs. For example, medical devices 111 may generate one or more user interfaces for users (e.g., patients)/medical professionals to view a user's blood flow metrics. The user interfaces may include one or more interactive displays, including colored visual indicators, graphics, charts, tables, comparisons to previous patient/user reports or population data, treatment recommendations, etc. The display may include indicators showing the progress of an analysis and/or indicators tracking the analyzed data. Medical devices 111 may prompt a notification (e.g., a message received at a user or medical professional's device) when a report is available for access. Alternately or in addition, medical devices 111 may display a user interface indicating, "report to be available in 3 days" or "please check back at 3 pm on Friday."

In one embodiment, medical devices 111 may also display a visual indicator on a user interface, showing that a user report has been accessed, either by the user or by a medical professional. For example, a medical professional may serve as a caretaker for "user A" and "user B." The medical professional may access a medical device 111 and see that user A has accessed her blood flow metrics data/logs and viewed her therapy recommendations for the afternoon. The medical professional may also access a medical device 111 and compare user B's current blood flow metrics (from the latest user B-specific blood flow simulation), to blood flow metrics calculated for user B earlier in the day. The medical professional may review or adjust therapy recommendations provided for user B, according to the progression of user B's health state throughout the day.

Network 113 may include the Internet, a content distribution network, or any other wired, wireless, and/or telephonic or local network. Sensors 101, medical data interfaces 103, the blood flow metrics platform 105, the data repository 107, the analytics platform 109, the medical devices 111, and various user and/or administrator devices may communicate with each other via network 113.

Wearable sensors 101, medical data interfaces 103, and/or medical devices 111 may include any type of electronic device configured to collect, send, and/or receive data, such as websites and multimedia content, over network 113. Devices may include medical devices, e.g., medical imaging devices, medical monitors, etc. Devices may also include one or more mobile devices, smartphones, personal digital assistants ("PDA"), tablet computers or any other kind of touchscreen-enabled device, a personal computer, a laptop, and/or server disposed in communication with network 113. Each of the devices may have a web browser and/or mobile browser installed for receiving and displaying electronic content received from one or more of web servers affiliated with blood flow monitoring system 100. The devices may include client devices that may have an operating system configured to execute a web or mobile browser, and any type of application, e.g., a mobile application. In one embodiment, various devices may be configured with network adapters to communicate data or analyzed reports over network 113. Alternatively, or additionally, various may be configured to transmit data or receive analyzed data over a local connection.

FIG. 2 is a block diagram 200 of the blood flow metrics platform 105 for computing blood flow metrics based on sensor data, according to an exemplary embodiment of the present disclosure. As shown in FIG. 2B, exemplary blood flow metrics platform 105 may include a control logic 201. Control logic 201 may direct the functions and interactions among the various modules and processors that may be operating as part of blood flow metrics platform 105.

In one embodiment, the health state module 203 and control logic 201 may determine various states of a user's health. The health state module 203 and control logic 201 may further determine a blood flow metric associated with the user that may provide an indication of the state of the user's health. The health state module 203 and control logic 201 may further determine ranges or threshold values for the blood flow metric that may indicate or characterize the various states. For example, the control logic 201 and health state module 203 may identify states of health as "ischemic" versus "healthy" using the blood flow metric, fractional flow reserve. In one such scenario, the control logic 201 and health state module 203 may determine that fractional flow reserve value less than 0.75-0.8 indicates that a user is experiencing myocardial ischemia, while a fractional flow reserve value of 1.0 or greater than 0.8 indicates that a user is healthy.

In another scenario, states of health may include "at risk for infarction" versus "healthy." In such a case, the control logic 201 and health state module 203 may determine a plaque vulnerability index, where a user may be "at risk for infarction" if the user's plaque vulnerability index value exceeds a threshold value or range. Depending on how the plaque vulnerability index is defined, the control logic 201 and health state module 203 the "at risk for infarction" range may alternately be if a plaque vulnerability index falls below a threshold value or range. The user may be considered "healthy" if his/her plaque vulnerability index value falls within a range deemed "healthy." The plaque vulnerability index may include a calculation/simulation of plaque stress versus material strength. The plaque vulnerability index may also include a calculated rupture risk. Other elements that may factor into a plaque vulnerability or rupture risk calculation may include plaque morphology, lumen surface geometry, erosion or inflammation in vessel(s), blood pressure, blood flow rate, blood viscosity or other chemical properties of the user's blood, location of the plaque in the vasculature, mechanical (stress/strain/tensile) properties of the plaque, vessel segment, or vessel wall, etc. In short, the control logic 201 and health state module 203 may determine the metrics needed to evaluate risk of infarction, as well as the thresholds or ranges of the metrics that may indicate whether a user is at risk, or not at risk.

Other health states may include "weight loss," "weight gain," or "stable weight maintained." Blood flow metrics that may indicate the weight changes may include nutrient flow in the portal vein, compared to metabolic demand. Another health state may include "vascular steal" versus "no vascular steal," and blood flow metric(s) that may indicate these states may include a comparison of blood flow magnitude/direction with a reference (e.g., normal) magnitude/direction. Yet another health state may include "hypertension" versus "healthy," where blood pressure may be the blood flow metric that indicates whether or not a user is experiencing hypertension.

In one embodiment, user state module 205 and control logic 201 may receive user sensor data and/or user medical data. Sensor or medical data may include heart rate, blood pressure, caloric burn rate, caloric intake, activity level, sweat level, body temperature, electrocardiogram, sleep amount/type/quality/time/etc., glucose level, cholesterol, urine test data, blood test data, body fat percentage, diet/ nutrition data (e.g., high sodium, high sodium, high caloric intake, low caloric intake, etc.), material properties of tissue (e.g., tissue strength, tensile strength, density, etc.). This data may all provide indications of the user's physiological state. Medical data may also include one or more anatomical models of the user's tissue or vasculature, images of the user's anatomy (e.g., computerized tomography scans, x-ray images, ultrasound images, intravascular images, angiography images, etc.). Medical data may further include the user's patient health information, including the user's patient medical history, prescriptions, allergies, physicians, medical histories or conditions of relatives of the user, etc. User state module 205 and control logic 201 may further receive user input, including symptoms (e.g., angina, lightheadedness, fainting, etc.) or physical state (e.g., inability to exercise or perform certain activities). User state module 205 and control logic 201 may also receive group (e.g., stored collective) data or demographic data, including age, weight, height, gender, ethnicity, location, insurance plan, or any medical data/health information/sensor information associated with or representative of members of the user's group or demographic.

In one embodiment, metrics selection module 207 and control logic 201 may select one or more blood flow computations to perform. In one embodiment, metrics selection module 207 and control logic 201 may determine one or more metrics to compute for a user. For example, if a user is at risk for heart disease, the metrics may include FFR, a perfusion index, or a plaque vulnerability/plaque rupture risk metric. If a user is trying to gain or lose weight, the metric to compute may include nutrient flow or metabolic demand. In one embodiment, the metrics selection module 207 and control logic 201 may select or determine metric(s) to compute for a user, depending on user input or input from a medical professional. Alternately or in addition, the metrics selection module 207 and control logic 201 may select or determine metrics to compute for a user, depending on sensors detected to be associated with a user. For instance, if a user is associated with sensor data of a treadmill, the metrics selection module 207 and control logic 201 may select nutrient flow and metabolic demand metrics to compute for the user, since the user may be trying to lose weight. In another instance, if a user is associated with sensor data of an heart rhythm monitoring device, the metrics selection module 207 and control logic 201 may select FFR as the metric to calculate for the user.

In one embodiment, computation module 209 and control logic 201 may compute a selected blood flow metric for a user, based on the received user sensor data, user medical data, and the selected blood flow computations. Blood flow metric calculations may include a series of flow equations that describe blood flow in the user-specific anatomical model. Calculating the value of a blood flow metric may include using a numerical method to solve three-dimensional equations of blood flow using a computer. The numerical method may be a known method, such as finite difference, finite volume, spectral, lattice Boltzmann, particle-based, level set, isogeometric, or finite element methods, or other computational fluid dynamics (CFD) numerical techniques. Calculating the value of a blood flow metric may further include machine learning, deep learning, or other techniques, for instance, as described in U.S. Patent Publication No. 2014/0073977 A1 filed May 16, 2013, hereby incorporated by reference in its entirety.

In some embodiments, blood may be modeled as a Newtonian, a non-Newtonian, or a multiphase fluid. Various factors may be taken into account for the calculations, including blood viscosity, blood vessel walls rigidity or compliance, vessel wall reactivity, vessel wall dynamics, etc. Several blood flow computation factors may be affected by physiological state. For example, vessels may change in size during different physiological states. In some cases, vessel size may change to accommodate more or less blood flow in response to signals from the sympathetic and parasympathetic nervous systems that regulate blood flow demand. Such changes mean that physiological state may dictate boundary conditions of blood flow simulations or calculations. Instances of simulating blood flow and estimating blood flow parameters/metrics under various physiological state conditions are described in U.S. Pat. No. 8,315,812 issued Nov. 20, 2012, U.S. Pat. No. 8,249,815 issued Aug. 21, 2012, U.S. Pat. No. 9,202,010 issued Dec. 1, 2015, all of which are hereby incorporated by reference in their entireties.

In one embodiment, the assessment module 211 and control logic 201 may interpret the user-specific computed value of the selected blood flow metric. For example, assessment module 211 and control logic 201 may infer a medical condition or state of health of the user, based on the computed value. In one embodiment, the assessment module 211 and control logic 201 may compare the computed user-specific blood flow metric(s) against the predetermined thresholds/ranges determined by the health state module 203 and control logic 201. The assessment module 211 and control logic 201 may determine, for instance, a health state for a user based on the comparison of the computed user-specific blood flow metric(s) and metrics defined by the health state module 203 and control logic 201.

In one embodiment, the notification module 213 and control logic 201 may initiate alerts based on results of the assessment module 211. For example, if a user is detected as being "at high risk for infarction," notification module 213 and control logic 201 may send an alert to a medical device to dispense medication and/or notify a medical professional. If a user is detected as being "at medium risk for infarction," notification module 213 and control logic 201 may provide an alert to the user and/or request a user input. Notification module 213 and control logic 201 may further provide reports and/or risk mapping from data generated by the assessment module 211, the computation module 209, the control logic 201, and/or the data repository 107. The notification module 213 and control logic 201 may generate any form of notification, display, representation, or output that may provide a user and/or medical professional with information on the user's state of health and medical condition. Various displays or representations are described in U.S. Pat. No. 8,315,812 issued Nov. 20, 2012, and U.S. Patent Publication No. 2015/0342537 filed Sep. 9, 2014, both of which are hereby incorporated by reference in their entireties.

FIG. 3 is a block diagram 300 of the analytics platform 109 for refining blood flow simulations based on sensor data, according to an exemplary embodiment of the present disclosure. As shown in FIG. 3, exemplary analytics platform 109 may include a control logic 301. Control logic 301 may direct the functions and interactions among the various modules and processors that may be operating as part of analytics platform 109.

In one embodiment, the user categorization module 303 and control logic 301 may determine one or more user groups. Exemplary user groups may include self-selected user groups. For example, users may provide input (e.g., using their wearable devices) indicating one or more social networks or users with which the user would like to be associated. Other categories for user groups may include the following: age, location, insurance policy, etc.

In one embodiment, sensor data categorization module 305 and control logic 301 may select sensor data to use for each blood flow metric computation. For example, the blood flow monitoring system 100 may include several sensors 101. Sensor data categorization module 305 and control logic 301 may detect a source of sensor data associated with a user, and determine which blood flow metric the sensor data may be used to compute. For example, sensor data categorization module 305 and control logic 301 may determine that blood pressure sensor data may be used to compute an FFR value for the user.

Alternately or in addition, sensor data categorization module 305 and control logic 301 may prioritize sensor data sources or identify preferred sensor data to use for each blood flow metric computation. For example, a metric for plaque vulnerability may be calculated from various factors, including blood pressure, blood flow rate, blood viscosity or other chemical properties of the user's blood. Sensor data categorization module 305 and control logic 301 may determine which data source or sensor data to use for the computation of each metric. For example, sensor data categorization module 305 and control logic 301 may determine that blood flow rates provided by a specialized blood flow sensor are preferable data sources over blood flow rates provided by a mobile app. Sensor data categorization module 305 and control logic 301 may then prompt calculations (e.g., by the blood flow metrics platform 105) to be computed using sensor data from the specialized blood flow sensor versus by the mobile app. As another example, sensor data categorization module 305 and control logic 301 may determine that one mobile app provides more reliable or more frequent blood pressure sensor data than a second app. The sensor data categorization module 305 and control logic 301 may also prompt blood flow metrics to be calculated from sensor data of the first app, over sensor data of the second app.

In one embodiment, model revision module 307 and control logic 301 may improve underlying assumptions and formulas used for calculations of the blood flow metrics. For example, model revision module 307 and control logic 301 may update blood flow calculation models, based on sensor data, user input, and stored data (including data associated with the user and/or data associated with individuals other than the user). For example, boundary conditions or material properties underlying blood flow calculation models may change as a user is in different physiological states. Model revision module 307 and control logic 301 may refine the blood flow calculation models. In some cases, model revision module 307 and control logic 301 may train machine learning or deep learning algorithms for computing blood flow metrics. For instance, if a user reports symptoms of ischemia or sensor data detects that a user may be experiencing symptoms of ischemia (e.g., heart palpitations), model revision model 307 and control logic 301 may adjust models for computing blood flow metrics, such that the models reflect possible ischemia for the user. For example in this case, model revision model 307 and control logic 301 may adjust boundary conditions of a blood flow model to reflect blood flow where the user may be experiencing ischemia. Alternately, if a user-specific anatomic model shows that a user may have atherosclerosis, but the user reports no symptoms of ischemia and sensor data also shows data within normal/health ranges, model revision model 307 and control logic 301 may adjust boundary conditions of a blood flow model to reflect healthy blood flow. As previously discussed, exemplary methods and systems of simulating blood flow under various physiological state conditions are described in U.S. Pat. No. 8,315,812 issued Nov. 20, 2012, U.S. Pat. No. 8,249,815 issued Aug. 21, 2012, U.S. Pat. No. 9,202,010 issued Dec. 1, 2015, all of which are hereby incorporated by reference in their entireties.

Alternately or in addition, model revision module 307 and control logic 301 may improve preliminary steps of computing blood flow metrics. For example, blood flow metrics may be determined based on user-specific anatomical models and flow simulations/calculations (e.g., physics-based models, reduced order models, lumped parameter models, etc.) based on the user-specific anatomical models. Model revision module 307 and control logic 301 may enhance user-specific anatomical models and flow simulations/calculations based on received sensor data or input from the user or other users. In some scenarios, the enhancements may take place over time, as sensor data or input is received from the user or other users over a span of time.

For example, model revision module 307 and control logic 301 may update the geometry of a user-specific anatomical model if sensor data of the user shows the user at a slightly above-normal activity state for most of the day. Such physiological characteristic sensor data may indicate that the user's vessels may be constricted, causing the user to show signs of an elevated activity level for extended periods of time. Model revision module 307 and control logic 301 may update the user-specific anatomical model, for instance, by narrowing the diameter of the vessels to reflect anatomy that would yield the sensor data. This time-varying user-specific anatomical model may be used as input to determine current and future values of blood flow metrics for the user.

In one embodiment, assessment revision module 309 and control logic 301 may enhance or train interpretation of computed blood flow metrics. For example, assessment revision module 309 and control logic 301 may update thresholds/ranges that may identify a user as being in one health state versus another. For instance, assessment revision module 309 and control logic 201 may adjust ranges or threshold values of the blood flow metric used by the blood flow metrics platform 105 to determine a user's medical condition(s). For example, if the blood flow metrics platform 105 sets an FFR value of 0.8 as indicating that a user is experiencing myocardial ischemia, but a user does not report (or render sensor data) indicating any symptoms of myocardial ischemia while the computed user-specific FFR value is 0.8, the assessment revision module 309 and control logic 301 may update the 0.8 threshold value to 0.75.

In some embodiments, assessment revision module 309 and control logic 301 may enhance or train interpretation of computed blood flow metrics may providing more refined interpretations of computed user-specific blood flow metrics. For example, the blood flow monitoring system 100 may initially set any FFR value of 0.75-0.8 as signaling that the user is at the health state, "user is experiencing myocardial ischemia." After collecting and aggregating data, the assessment revision module 309 and control logic 301 may determine that FFR value of 0.8 indicates "at risk of myocardial ischemia," and an FFR value of 0.75 indicates "user is in danger." The collected and aggregated data may include user-specific data. In other words, the refinements or updated interpretations of the assessment revision module 309 and control logic 301 may be user-specific. For one user, the assessment revision module 309 and control logic 301 may determine that the user is not in a dangerous medical condition until the user's FFR value is at 0.75. For a second user, the assessment revision module 309 and control logic 301 may determine that the second user is experiencing a dangerous medical condition when the user's FFR value is at 0.82. Alternately or in addition, the collected and aggregated data may include data associated with individuals other than the user. In some cases, the individuals may be any individuals monitored by the blood flow monitoring system. In other embodiments, the individuals may include individuals that are associated with the user, for example, the individuals may be biologically related to the user. Alternately or in addition, the individuals may be categorized with the user based on similarities with the user in demographics, health conditions, medical plans, hospital locations, physicians, sensor data type, etc.

In one embodiment, the notification revision module 311 and control logic 301 may train, set, and/or adjust prompts in reaction to assessments. For example, the notification revision module 311 and control logic 301 may adjust dosage amounts based on user input or sensor data following user intake of medication. The notification revision module 311 and control logic 301 may also update responses as the assessment revision module 309 and control logic 301 refine assessments. For example, the blood flow monitoring system 100 may initially prompt a doctor anytime a user's FFR value falls below 0.8. Over time, the notification revision module 311 and control logic 301 may determine that, for a particular user, an FFR value of 0.8 triggers a notification to the user to monitor his/her activities and diet and doctor is not notified unless the user's FFR value falls to 0.75.

In one embodiment, the population data module 313 and control logic 301 may aggregate data for analytics. For example, the population data module 313 and control logic 301 may perform risk mapping and use data output from the blood flow metrics platform 105 and data repository 107 to provide comparisons for the blood flow metrics platform 105 and/or medical devices 111. For example, the population data module 313 and control logic 301 may determine users that are most responsive to a particular treatment. The population data module 313 and control logic 301 may then identify characteristics that the users may share so that predictions may be made for a future user, or for a current user at a different point in time.

For example, the population data module 313 and control logic 301 may determine that users living in urban areas are more responsive to exercise regimens than users living in rural areas. Such correlation may enhance treatment planning for a new user, or for a monitored user that may move to different locations through his/her lifetime. For example, treatment recommendations may be adjusted such that exercise regimens may be suggested to urban users, while dietary changes or medications may be suggested to rural users. The population data module 313 and control logic 301 may further coordinate with the sensor data categorization module 305, model revision module 307, assessment revision module 309, and/or notification revision module 311 to improve user analysis using collective data gathered from other users, empirical data, research data, etc.

FIG. 4 is a flow diagram of an exemplary method for initializing a blood flow model of a user or determining a user's initial conditions, including the user's blood flow characteristic(s) or tissue characteristic(s) at an initial point in time. The exemplary initialization method of FIG. 4 further includes determining a user's medical conditions or health state at a first point in time. FIG. 5 is a flow diagram of an exemplary method for determining a user's blood flow characteristic(s) or tissue characteristic(s) at a point in time after the initial point in time. In particular, the method of FIG. 5 updates the user's blood flow characteristic(s) or tissue characteristic(s) using sensor data received after the initial point in time. FIG. 5 also describes determining a change to the user's medical condition or state of health using the sensor data, so that a user's medical condition may be monitored based on the sensor data.

Figure 6A:
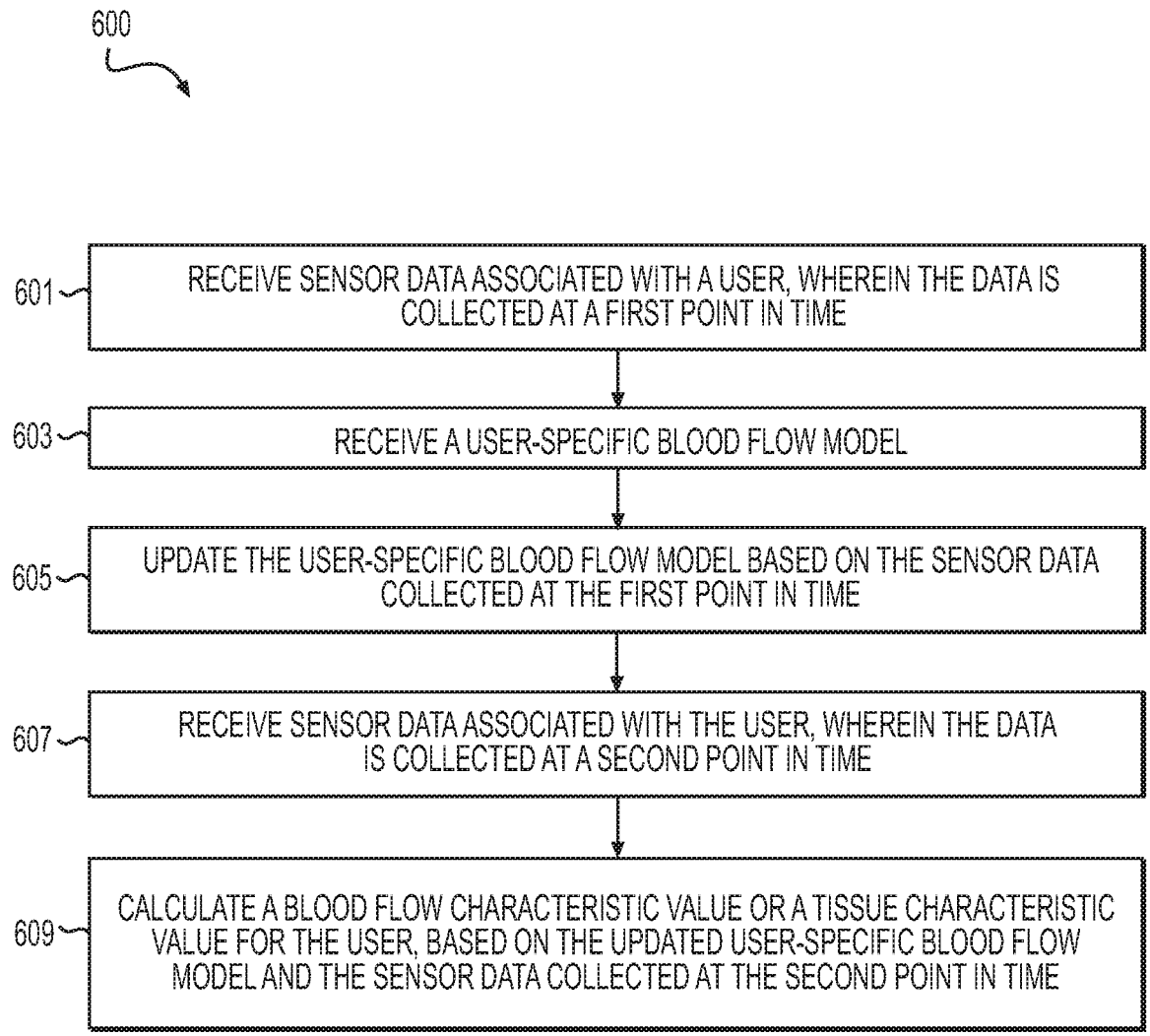
FIGS. 6A and 6B are flow diagrams of determining updates to blood flow model(s), based on user-specific activity data, according to an exemplary embodiment of the present disclosure.
Figure 6B:
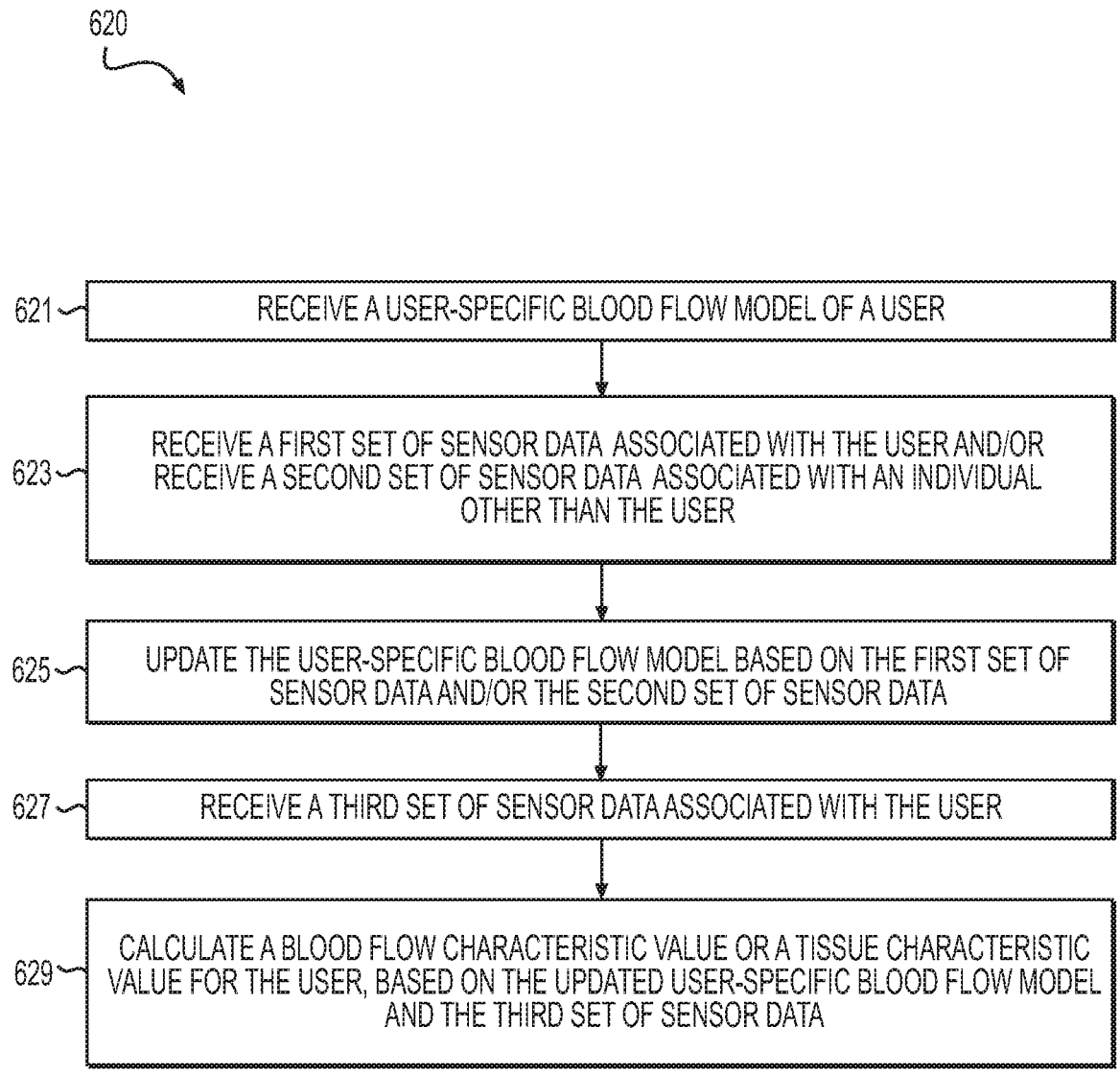

In addition to using sensor data to update or track a user's blood flow characteristic(s) or tissue characteristic(s), sensor data may be used to update blood flow models underlying calculations of the blood flow characteristic(s) or tissue characteristic(s). FIGS. 6A and 6B describe exemplary updates to the user's blood flow model, based on the sensor data. FIG. 6A includes an exemplary method for updating the blood flow model over time, based on sensor data collected for a particular user. For example, a blood flow model may be constructed based on user-specific boundary condition(s) or a user-specific anatomic model. Sensor data of the user collected over time may result in a modification to the user-specific boundary condition(s) or the user-specific anatomic model. Such modifications are described in more detail in FIG. 6A. FIG. 6B includes an exemplary method for updating a blood flow model, based on sensor data associated with individuals other than the user. For example, blood flow models may be refined from sensor data collected from individuals similar to the user, either in age, height, weight, medical history, location, etc.

FIG. 4 is a flow diagram of an exemplary method 400 of initializing a blood flow model of a user, where the blood flow model incorporates real-time sensor data, according to an exemplary embodiment. The method of FIG. 4 may be performed by the blood flow metrics platform 105, based on data received from sensors 101 over electronic network 113. Method 400 may be performed using a processor (e.g., laptop, desktop, cloud computing architecture, graphics processing unit (GPU), digital signal processor (DSP), mobile phone, tablet, etc.).

In one embodiment, step 401 may include receiving a user-specific anatomical model of at least a portion of the user vasculature in an electronic storage medium (e.g., hard drive, network drive, smart phone, tablet, cloud drive, etc.). Exemplary user vasculature may include: coronary vasculature, peripheral vasculature, cerebral vasculature, renal vasculature, visceral vasculature, hepatic vasculature, a portal vein, etc. Alternately or in addition, step 401 may include receiving a user-specific anatomical model of at least a portion of tissue being supplied by the vasculature represented by the anatomical model. Exemplary tissue being supplied by vasculature represented by the anatomical model may include: myocardial heart tissue, muscles in the peripheral aspects of the body, brain tissue, kidney tissue, or tissue of other internal organs, including the liver, stomach, spleen, intestines, colon, lungs, pancreas, etc.

In one embodiment, step 403 may include receiving an initial set of physiological characteristics of the user-specific anatomic model (e.g., the user-specific anatomic model of step 401). The initial set of physiological characteristics may include characteristics of the user at an initial physiological state, and/or a physiological state associated with the received user-specific anatomical model. Exemplary user physiological characteristics may include values of heart rate, diastolic or systolic blood pressure, caloric burn rate, caloric intake, activity level, sweat level, body temperature, electrocardiogram metrics (e.g., including the user's heartbeat), sleep amount and/or type, glucose level(s), cholesterol, urine test(s), body fat percentage, diet/nutrition (e.g., high sodium or low sodium diet), material properties of tissue (including tissue strength, tensile strength, density, etc.).

In one embodiment, the initial set of user physiological characteristics may be population-based averages or learned from prior user data/characteristics. Alternately or in addition, the initial set of physiological characteristics may be received from one or more sensors. For instance, the sensors may be sensors of wearable, medical, or home health devices with a user. Exemplary devices include: heart rate monitors, Holter monitors, pacemakers, or other heart rhythm monitoring devices, phones, smart watches, blood pressure cuffs, accelerometers (e.g., in a smart phone or watch), exercise equipment (e.g., treadmills, stationary bikes, ellipticals, etc.), bathroom scales, smart toilets, sleep monitors, glucose monitors, insulin pumps, smartphone applications (e.g., apps logging sleep, exercise, diet, food intake, fertility cycles, etc.), etc.

In one embodiment, step 405 may include determining the user's initial blood flow characteristic or initial tissue characteristic, based on the user-specific anatomical model and the initial set of physiological characteristics. In one embodiment, the user-specific anatomical model of the user's vasculature and/or the user-specific anatomic model of the user's tissue may be used to determine the user's initial blood flow characteristic or initial tissue characteristic. In one embodiment, the initial blood flow characteristic and/or initial tissue characteristics may be calculated using one or more of: a steady state or time-based physics based model, a model based on machine learning, or an image-driven model (e.g., using contrast intensity gradients to calculate blood flow, transluminal attenuation gradient (TAG), etc.), any non-physical model, etc. Blood flow characteristics or tissue characteristics at one or more locations in the user's-specific anatomical model may include: blood pressure, blood flow magnitude and/or direction, blood flow shear stress and/or axial stress, concentration of nutrients, drugs, etc., blood sufficiency at one or more tissue locations, material stress/strain (e.g., stress/strain of tissue or vessel wall(s)), comparison of one or more of these blood flow characteristics at two or more locations, etc.

In one embodiment, step 407 may include defining one or more threshold values of blood flow characteristic(s) or tissue characteristic(s), where each threshold value is associated with a health state or medical condition. For example, step 407 may include defining a plurality of health states or medical conditions, including ischemia, hypertension, hyperemia, hypothermic, etc.). Step 407 may further include determining or defining one or more indications of health. For example, indications may include blood flow characteristics that may show that a user is experiencing ischemia, hypertension, risk or prognosis for infarction, weight loss/gain, vascular steal phenomenon, etc. In some cases, step 407 may include determining a blood flow characteristic or tissue characteristic associated with each health state. For instance, step 407 may include determining a threshold value defining a point at which a user may be classified as being in one state of health versus another.

In one embodiment, a comparison of a user-specific calculated blood flow characteristic or a user-specific calculated tissue characteristic against the threshold value may indicate a state of health of the user. For example, ischemia may be evidenced by fractional flow reserve (FFR), coronary flow reserve (CFR), etc. As another example, hypertension may be evidenced by blood pressure; risk or prognosis for infarction may be shown by plaque vulnerability, as evidenced by plaque stress compared to strength or calculated rupture risk. As yet another instance, weight loss or weight gain may be evidenced by nutrient flow in the portal vein compared to metabolic demand. Furthermore, vascular steal syndrome may be evidenced by a comparison of blood flow magnitude/direction with a reference normal magnitude/direction.

In one embodiment, step 409 may include comparing the user's initial blood flow characteristic or initial tissue characteristic (e.g., of step 405) to a corresponding threshold value (e.g., of step 407) to determine an initial health state of the user. For example, step 409 may include determining whether the user is ischemic or not ischemic in a particular tissue or portion of tissue, hypertensive or non-hypertensive, at risk of vulnerable plaque, losing weight or gaining weight, at risk for infarction, experiencing vascular steal or no vascular steal, etc.

In one embodiment, steps 407 and 409 may further include determining a user tissue characteristic if the received initial data includes a user blood flow characteristic, or in the converse, determining a user blood flow characteristic if the received initial data includes a tissue characteristic. For example, if a received user blood flow characteristic includes blood flow rate, steps 407 and 409 may include using the received user blood rate to determine a tissue characteristic of a perfusion index for the user. Alternately or in addition, if a received user tissue characteristic includes a measure of tissue conductivity, steps 407 and 409 may include using the user's tissue conductivity measurement to determine a blood flow characteristic of blood supply or blood flow rate for the user. Either the user blood flow characteristic and/or the user tissue characteristic may be used to determine the user's initial health state.

FIG. 5 is a flow diagram of an exemplary method 500 of determining a user's state of health in a real-time basis using sensor data, according to an exemplary embodiment. The method of FIG. 5 may be performed by the blood flow metrics platform 105, based on data received from sensors 101 over electronic network 113. Method 500 may be performed using a processor (e.g., laptop, desktop, cloud computing architecture, graphics processing unit (GPU), digital signal processor (DSP), mobile phone, tablet, etc.).

In one embodiment, step 501 may include associating a user with one or more sensors. In one embodiment, the sensors may be sensors of wearable, medical, or home health devices associated with a user. Examples of such wearable, medical, or home health devices may include heart rate monitors, Holter monitors, pacemakers, or other heart rhythm monitoring devices, phones, smart watches, blood pressure cuffs, accelerometers (e.g., in a smart phone or watch), exercise equipment (e.g., treadmills, stationary bikes, ellipticals, etc.), bathroom scales, smart toilets, sleep monitors, glucose monitors, insulin pumps, smartphone applications (e.g., apps logging sleep, exercise, diet, food intake, fertility cycles, etc.), etc. Alternately or in addition, step 501 may include associating a user with other data generated from wearable, medical, or home health devices. For example, a user may have a CT performed at a hospital, be given a device, and then exercise on a treadmill. In such an instance, step 501 may including receiving the CT data and device-collected activity data for an initial simulated exercise test.

In one embodiment, step 503 may include receiving data from the one or more sensors and/or wearable, medical, or home health devices associated with the user. In one embodiment, step 503 may be performed automatically upon detection of a sensor, device, and/or app associated with a user. Alternately or in addition, step 503 may be performed by a user. For example, step 503 may include receiving user input regarding the user's condition. In one instance, the input may be received automatically from the sensor, device, or app. In another instance, the user may enter the data (e.g., from a device, website, wearable, phone, watch, etc.). The user input may be based on physician observation, self-reports, prior conditions, etc. User input may include a symptom (e.g., angina, light-headedness, fainting, etc.) or a physical state (e.g., an inability to exercise or perform an activity.

In some cases, step 503 may include generating a prompt seeking user input, where the user may provide the input in response to the prompt. The prompt may be generated upon receiving sensor, device, and/or app data that may correspond to certain symptoms or conditions that the user may be experiencing, given the received sensor/device/app data. For example, glucose meter sensor data may indicate that a user has low blood sugar, or a heart rate monitor may show that a user has an unusual heart rhythm. Step 503 may include detecting the abnormality and prompting the user to respond or enter his/her current symptom(s) or condition.

In one embodiment, step 505 may include determining one or more user physiological characteristics, based on the received sensor data. Exemplary user physiological characteristics may include values of heart rate, diastolic or systolic blood pressure, caloric burn rate, caloric intake, activity level, sweat level, body temperature, electrocardiogram metrics (e.g., including the user's heartbeat), sleep amount and/or type, glucose level(s), cholesterol, urine test(s), body fat percentage, diet/nutrition (e.g., high sodium or low sodium diet), material properties of tissue (including tissue strength, tensile strength, density, etc.). Step 505 may further include determining or adjusting the one or more user physiological characteristics based on user input.

In one embodiment, step 507 may include receiving the user-specific anatomical model (e.g., of step 401), as well as either a threshold value of a blood flow characteristic or a threshold value of a tissue characteristic (e.g., of step 403). In some cases, step 507 may also include receiving the initial health state of the user (e.g., of step 405).

In one embodiment, step 509 may include calculating a second user-specific blood flow characteristic or a second user-specific tissue characteristic based on the received data (e.g., of step 503), the user physiological characteristic (e.g., of step 505), and the user-specific anatomic model (e.g., of step 507). Blood flow characteristics or tissue characteristics at one or more locations in the user's-specific anatomical model may include: blood pressure, blood flow magnitude and/or direction, blood flow shear stress and/or axial stress, concentration of nutrients, drugs, etc., blood sufficiency at one or more tissue locations, material stress/strain (e.g., stress/strain of tissue or vessel wall(s)), comparison of one or more of these blood flow characteristics at two or more locations, etc.

In one embodiment, step 509 may further include refining the received user-specific anatomic model of step 507, based on the physiological characteristics determined from the received data. For example, if a user is determined to be in an exercise state, step 509 may include updating the received user-specific anatomic model to reflect the exercise state and further calculating the second user-specific blood flow characteristic or the second user-specific tissue characteristic using the updated user-specific anatomic model. For instance, if the original user-specific anatomic model reflected a user's vasculature at a baseline/rest state, updating the model to reflect an exercise state may include dilating the vessels of the model. Analyses used to calculated the second user-specific blood flow characteristic or the second user-specific tissue characteristic may also be modified based on the received user physiological characteristics of step 505. For example, in the above instance of a user changing from a rest state to an exercise state, the blood flow characteristic or tissue characteristic calculations may include boundary conditions comprising lower resistance.

The modifications to the user-specific anatomic model and the blood flow/tissue analyses may be further adjusted based on user input. For an instance involving ischemia, for example, step 509 may include updating a model of user-specific blood flow to reflect ischemia and further adjusting the model based on the user's input symptoms. For example, the model of user-specific blood flow may include the geometry of user's vascular anatomy being narrowed (relative to the user's expected/healthy vascular anatomy, or the user's anatomy at an earlier point in time). If a user reports feeling discomfort or tightness in his/her chest (e.g., in response to a prompt for user input), the model of user-specific blood flow may be updated to show further narrowing of the modeled vessels. If a user reports an absence of symptoms, the updated model of user-specific blood flow may be maintained, without further narrowing of the modeled vasculature. As another example, a model of user-specific plaque rupture risk may be changed based on events described or input by users. For example, a user-specific blood flow model may be updated if a user experiences a heart attack or stroke, or any other event reported by the user.

In one embodiment, step 511 may include determining a second medical condition associated with the user, given the sensor data or the user physiological characteristics determined from the sensor data. In one embodiment, step 511 may include comparing the calculated user-specific blood flow characteristic (e.g., of step 509) to the threshold value of the blood flow characteristic (e.g., of step 403) to determine the user's second medical condition. Alternately or in addition, step 511 may include comparing the calculated user-specific tissue characteristic (e.g., of step 509) to the threshold value of the tissue characteristic (e.g., of step 403) to determine the user's second medical condition.

In one embodiment, step 513 may include updating the initial state of health (e.g., of step 409), based on the determined second medical condition (e.g., of step 511). In one embodiment, step 513 may include determining a difference between the initial health state of the user and the second health state of the user, and generating an alert or new report based on the second health state of the user. In one embodiment, the alert or report may be transmitted to the medical devices 111, the user, a physician, a hospital network, an insurance provider, a health care professional. Alternately or in addition, the alert and/or report may be stored in an electronic storage medium. In one embodiment, step 513 may include further generating a prompt for input from the user, in response to the second health state. For example, if a user is determined to be in a second health state of high likelihood of ischemia, step 513 may include initiating a prompt to request an input from the user. This prompt may be used to check that a user is still responsive, or whether the user is experiencing a dangerous health event (e.g., an ischemic stroke).

FIGS. 6A and 6B describe updating blood flow models underlying the calculations of the user-specific blood flow characteristic(s) or user-specific tissue characteristic(s). In some embodiments, the methods described in these figures may be performed multiple times, e.g., resulting in an increasingly refined user-specific blood flow model. In one embodiment, the methods described in FIGS. 6A and 6B may be performed continuously as more sensor data is received, and/or periodically (e.g., at pre-set time intervals, or upon indication that a user's physiological state may be in flux).

FIG. 6A is a flow diagram of an exemplary method 600 of updating a user-specific blood flow model using user-specific activity data from sensor data, according to an exemplary embodiment. The method of FIG. 6A may be performed by the analytics platform 109, based on data received from sensors 101 over electronic network 113. Method 600 may be performed using a processor (e.g., laptop, desktop, cloud computing architecture, graphics processing unit (GPU), digital signal processor (DSP), mobile phone, tablet, etc.).

In one embodiment, step 601 may include receiving sensor data associated with a user, wherein the sensor data is collected at a first point in time. In one embodiment, step 603 may include receiving a user-specific blood flow model. The user-specific blood flow model may include a user-specific boundary condition and/or a user-specific anatomic model. A boundary condition may provide information about an anatomic or blood flow model at certain boundaries (e.g., inflow boundaries, outflow boundaries, vessel wall boundaries, etc. Each boundary may include a prescribed value or field for blood flow velocity, blood flow rate, or blood pressure, for instance. In one embodiment, step 605 may include updating the user-specific blood flow model based on the sensor data collected at the first point in time. For instance, step 605 may include receiving sensor data indicating a blood flow rate or heart rate "x" at the first point in time. Step 605 may include determining that the blood flow rate or heart rate value of "x" indicates a vessel diameter of or blood flow velocity value of "y." In this way, step 605 may include updating or determining a blood flow model for a user at the first point in time, the blood flow model incorporating a user-specific anatomical model with a vessel diameter or a user-specific boundary condition with a value of "y."

In one embodiment, step 607 may include receiving sensor data associated with the user, the sensor data being collected at a second point in time. Step 609 may then include calculating a blood flow characteristic value or a tissue characteristic value for the user at the second point in time, based on the updated user-specific blood flow model and the sensor data collected at the second point in time. For example, step 609 may use the blood flow model incorporating a user-specific anatomical model with a vessel diameter or a user-specific boundary condition with a value of "y" to calculate the blood flow characteristic value or the tissue characteristic value for the user at the second point in time.

FIG. 6B is a flow diagram of an exemplary method 620 of determining a user's state of health in a real-time basis using sensor data, according to an exemplary embodiment. The method of FIG. 6B may be performed by the analytics platform 109, based on data received from sensors 101 over electronic network 113. Method 620 may be performed using a processor (e.g., laptop, desktop, cloud computing architecture, graphics processing unit (GPU), digital signal processor (DSP), mobile phone, tablet, etc.).

In one embodiment, step 621 may including receiving a user-specific blood flow model. The blood flow model may include a user-specific boundary condition and/or a user-specific anatomic model. In one embodiment, step 623 may include receiving sensor data associated with an individual other than the user. For example, the individual may share one or more user characteristics with the user (e.g., age, medical history, health state, medical condition(s), etc.). In one embodiment, step 623 may further include accessing stored sensor data associated with the user. Stored sensor data may include sensor data previously collected from the user. Step 625 may include updating the received user-specific blood flow model using the sensor data associated with the individual and/or the user's stored sensor data.

In one embodiment, step 627 may include receiving sensor data associated with the user. This sensor data may include sensor data collected later than the collection time of the sensor data associated with the individual and/or the user's stored sensor data. In one embodiment, step 629 may include calculating a blood flow characteristic value or a tissue characteristic value for the user, based on the updated user-specific blood flow model and the received sensor data associated with the user.

The present disclosure includes a system and method for providing blood flow metric-based health assessments using user-specific activity data. In one embodiment, the user-specific activity data may be provided by ongoing sensor data from wearable devices. The present disclosure further includes a system and method which may use user-specific activity data to update blood flow or user health assessment models and/or algorithms. Accordingly, the disclosed system and method may provide up-to-date analyses and predictions of a user's medical condition, as supplemented by the user's most current physiological state. The disclosed system and method may further provide constantly-updated diagnostic data and predictions for a user, including computation methods that are updated based on the user's tracked sensor data and the physiological state that a user's body may be in at the time of the provided sensor data.

Any of the described embodiments may be modified, for example, to include variations of data that may be kept within a region. The disclosed systems and methods may be modified to model and assess any range of changes to circulation.

Program aspects of the technology may be thought of as "products" or "articles of manufacture" typically in the form of executable code and/or associated data that is carried on or embodied in a type of machine readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of calculating blood flow metrics using sensor data, the method comprising:
   receiving or accessing a user-specific anatomical model and a first set of physiological characteristics of a user;
   computing or receiving first values of a plurality of blood flow metrics of the user based on the user-specific anatomical model and the first set of physiological characteristics;
   detecting a sensor of a wearable device associated with the user;
   based on the detected sensor, selecting at least one of the plurality of blood flow metrics;
   receiving sensor data from the detected sensor, the sensor data comprising activity data of the user's blood flow or the user's physiological characteristics over a period of time in which the user performed an activity; and
   computing a second value of the selected blood flow metric of the user based on the user-specific anatomical model and the activity data.

2. The computer-implemented method of claim 1, further comprising:
   determining a blood flow model to use to compute the second value of the selected blood flow metric; and
   updating the blood flow model based on the received sensor data.

3. The computer-implemented method of claim 2, wherein the blood flow model is based on a user-specific boundary condition, and updating the blood flow model comprises updating the user-specific boundary condition based on the sensor data.

4. The computer-implemented method of claim 2, wherein the blood flow model is based on the user-specific anatomical model, and updating the blood flow model comprises updating the user-specific anatomical model based on the sensor data.

5. The computer-implemented method of claim 1, further comprising:
   receiving stored sensor data associated with the user, wherein the stored sensor data is collected at a first point in time prior to collection of the sensor data of the user's blood flow or collection of the sensor data of the user's physiological characteristics;
   determining a blood flow model based on the stored sensor data; and
   computing the second value of the selected blood flow metric of the user further based on the determined blood flow model.

6. The computer-implemented method of claim 1, further comprising:
   receiving stored sensor data associated with an individual other than the user;
   determining a blood flow model based on the stored sensor data; and
   computing the second value of the second blood flow metric of the user further based on the determined blood flow model.

7. The computer-implemented method of claim 6, further comprising:
   identifying a user group associated with the user; and
   identifying the individual based on the user group associated with the user.

8. The computer-implemented method of claim 1, further comprising:
   based on the selected blood flow metric, selecting which sensor data to use for the computing the second value.

9. A system for calculating blood flow metrics using sensor data, the system comprising:
   at least one data storage device storing instructions of calculating blood flow metrics using sensor data; and
   at least one processor configured to execute the instructions to perform a method including:
      receiving or accessing a user-specific anatomical model and a first set of physiological characteristics of a user;
      computing or receiving first values of a plurality of blood flow metrics of the user based on the user-specific anatomical model and the first set of physiological characteristics;
      detecting a sensor of a wearable device associated with the user;
      based on the detected sensor, selecting at least one of the plurality of blood flow metrics;
      receiving sensor data from the detected sensor, the sensor data comprising activity data of the user's blood flow or the user's physiological characteristics over a period of time in which the user performed an activity; and
      computing a second value of the selected blood flow metric of the user based on the user-specific anatomical model and the activity data.

10. The system of claim 9, wherein the system is further configured for:
    determining a blood flow model to use to compute the second value of the selected blood flow metric; and
    updating the blood flow model based on the received sensor data.

11. The system of claim 10, wherein the blood flow model is based on a user-specific boundary condition, and updating the blood flow model comprises updating the user-specific boundary condition based on the sensor data.

12. The system of claim 10, wherein the blood flow model is based on the user-specific anatomical model, and updating the blood flow model comprises updating the user-specific anatomical model based on the sensor data.

13. The system of claim 9, wherein the system is further configured for:
    receiving stored sensor data associated with the user, wherein the stored sensor data is collected at a first point in time prior to collection of the sensor data of the user's blood flow or collection of the sensor data of the user's physiological characteristics;
    determining a blood flow model based on the stored sensor data; and
    computing the selected second value of the blood flow metric of the user further based on the determined blood flow model.

14. The system of claim 13, where the system is further configured for:
    receiving stored sensor data associated with an individual other than the user;

determining a blood flow model based on the stored sensor data; and computing the selected second value of the blood flow metric of the user further based on the determined blood flow model.

15. The system of claim 14, wherein the system is further configured for:

identifying a user group associated with the user; and identifying the individual based on the user group associated with the user.

16. The system of claim 9, wherein the system is further configured for:

based on the selected blood flow metric, selecting which sensor data to use for the computing the second value.

17. A non-transitory computer readable medium for use on a computer system containing computer-executable programming instructions for performing a method of calculating blood flow metrics using sensor data, the method comprising:

receiving or accessing a user-specific anatomical model and a first set of physiological characteristics of a user;

computing or receiving first values of a plurality of blood flow metrics of the user based on the user-specific anatomical model and the first set of physiological characteristics;

detecting a sensor of a wearable device associated with the user;

receiving sensor data from the detected sensor, the sensor data comprising activity data of the user's blood flow or the user's physiological characteristics over a period of time in which the user performed an activity;

based on the detected sensor, selecting which of the plurality of blood flow metrics to calculate; and computing a second value of the selected blood flow metric of the user based on the user-specific anatomical model and the activity data.

18. The non-transitory computer readable medium of claim 17, the method further comprising:

determining a blood flow model to use to compute the second value of the selected blood flow metric; and updating the blood flow model based on the received sensor data.

19. The non-transitory computer readable medium of claim 18, wherein the blood flow model is based on a user-specific boundary condition, and updating the blood flow model comprises updating the user-specific boundary condition based on the sensor data.

20. The non-transitory computer readable medium of claim 18, wherein the blood flow model is based on the user-specific anatomical model, and updating the blood flow model comprises updating the user-specific anatomical model based on the sensor data.

* * * * *